United States Patent
Beeharry et al.

(10) Patent No.: US 11,166,944 B2
(45) Date of Patent: *Nov. 9, 2021

(54) APILIMOD COMPOSITIONS AND METHODS FOR USING SAME IN THE TREATMENT OF RENAL CANCER

(71) Applicant: AI Therapeutics, Guilford, CT (US)

(72) Inventors: Neil Beeharry, Guilford, CT (US); Sophia Gayle, East Haven, CT (US); Sean Landrette, Meriden, CT (US); Paul Beckett, Yorktown Heights, NY (US); Chris Conrad, Guilford, CT (US); Tian Xu, Shanghai (CN); Jonathan M. Rothberg, Guilford, CT (US); Henri Lichenstein, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/695,814

(22) Filed: Nov. 26, 2019

(65) Prior Publication Data

US 2020/0297706 A1    Sep. 24, 2020

Related U.S. Application Data

(63) Continuation of application No. 16/226,175, filed on Dec. 19, 2018, now abandoned, which is a continuation of application No. 15/524,844, filed as application No. PCT/US2015/059512 on Nov. 6, 2015, now Pat. No. 10,206,910.

(60) Provisional application No. 62/077,127, filed on Nov. 7, 2014.

(51) Int. Cl.
  *A61K 31/44* (2006.01)
  *A61K 31/506* (2006.01)
  *A61K 31/5377* (2006.01)
  *A61K 45/06* (2006.01)
  *A61K 9/00* (2006.01)

(52) U.S. Cl.
  CPC ............ *A61K 31/44* (2013.01); *A61K 9/0019* (2013.01); *A61K 31/506* (2013.01); *A61K 31/5377* (2013.01); *A61K 45/06* (2013.01); *A61K 2300/00* (2013.01)

(58) Field of Classification Search
  CPC ... A61K 31/44; A61K 31/506; A61K 31/5377
  See application file for complete search history.

(56) References Cited

U.S. PATENT DOCUMENTS

| | | |
|---|---|---|
| 5,210,015 A | 5/1993 | Gelfand et al. |
| 5,487,972 A | 1/1996 | Gelfand et al. |
| 6,660,733 B2 | 12/2003 | Sun et al. |
| 6,693,097 B2 | 2/2004 | Ono et al. |
| 6,858,606 B2 | 2/2005 | Sun et al. |
| 7,745,436 B2 | 6/2010 | Kostik et al. |
| 7,863,270 B2 | 1/2011 | Demko et al. |
| 7,923,557 B2 | 4/2011 | Zhang et al. |
| 9,295,731 B2 | 3/2016 | Nguyen |
| 10,179,135 B2 | 1/2019 | Lichenstein et al. |
| 10,206,910 B2 | 2/2019 | Beeharry et al. |
| 10,350,213 B2 | 7/2019 | Lichenstein et al. |
| 10,765,682 B2 | 9/2020 | Beeharry et al. |
| 2007/0112005 A1 | 5/2007 | Chen et al. |
| 2007/0149521 A1 | 6/2007 | Crew et al. |
| 2007/0254883 A1 | 11/2007 | Crew et al. |
| 2009/0312319 A1 | 12/2009 | Ren et al. |
| 2010/0015140 A1 | 1/2010 | Danter |
| 2010/0048547 A1 | 2/2010 | Atallah et al. |
| 2011/0081338 A1 | 4/2011 | Roberts et al. |
| 2011/0277018 A1 | 11/2011 | Weizman |
| 2011/0287018 A1 | 11/2011 | Bosch |
| 2013/0267521 A1 | 10/2013 | Castro et al. |
| 2014/0105891 A1 | 4/2014 | Garmey et al. |
| 2017/0007613 A1 | 1/2017 | Lichenstein et al. |
| 2017/0020884 A1 | 1/2017 | Lichenstein et al. |
| 2017/0333408 A1 | 11/2017 | Beeharry et al. |
| 2017/0333439 A1 | 11/2017 | Beeharry et al. |
| 2017/0333498 A1 | 11/2017 | Beeharry et al. |
| 2018/0015098 A1 | 1/2018 | Lichenstein et al. |
| 2018/0078561 A1 | 3/2018 | Beckett et al. |
| 2019/0183902 A1 | 6/2019 | Lichenstein et al. |
| 2019/0201385 A1 | 7/2019 | Beeharry et al. |
| 2019/0209576 A1 | 7/2019 | Beeharry et al. |
| 2020/0268764 A1 | 8/2020 | Lichenstein et al. |
| 2021/0077500 A1 | 3/2021 | Landrette et al. |

FOREIGN PATENT DOCUMENTS

| | | |
|---|---|---|
| CN | 102905707 A | 1/2013 |
| CN | 106659716 A | 5/2017 |
| EA | 009873 B1 | 4/2008 |
| JP | 2007-532667 A | 11/2007 |

(Continued)

OTHER PUBLICATIONS

Dutcher, J.P. Ther. Adv. Urol., 2013, vol. 5, No. 6, pp. 338-353.*
Baird, A.M. et al., (Jun. 19, 2013). "IL-23R is Epigenetically Regulated and Modulated by Chemotherapy in Non-Small Cell Lung Cancer." Frontiers in Oncology, vol. 3:1-9, Article 162.
Cai, X. et al., (Jul. 25, 2013). "PIKfyve, a Class III PI Kinase, is the Target of the Small Molecular IL-12/IL-23 Inhibitor Apilimod and a Player in Toll-Like Receptor Signaling." Chemistry & Biology, vol. 20(7): 912-921..
Chou, T-C. et al., (2010; Published Online Jan. 12, 2010) "Drug combination studies and their synergy quantification using the Chou-Talalay method." Cancer Research 70:440-446.

(Continued)

*Primary Examiner* — Samira J Jean-Louis

(74) *Attorney, Agent, or Firm* — Muriel Liberto, Esq.; Mintz Levin Cohn Ferris Glovsky and Popeo, P.C.

(57) ABSTRACT

The present disclosure relates to methods for treating renal cancer with apilimod and related compositions and methods.

11 Claims, 22 Drawing Sheets

(56) References Cited

FOREIGN PATENT DOCUMENTS

| | | |
|---|---|---|
| JP | 2009-209069 A | 9/2009 |
| JP | 2013-522212 A | 6/2013 |
| JP | 2013-542980 A | 11/2013 |
| MX | 2016009590 A | 5/2017 |
| RU | 2 438 664 C2 | 1/2012 |
| RU | 2 486 183 C9 | 1/2014 |
| RU | 2013110124 A | 9/2014 |
| WO | 95/13399 A1 | 5/1995 |
| WO | 2005/076843 A2 | 8/2005 |
| WO | 2005/112938 A2 | 12/2005 |
| WO | 2005/076843 A3 | 1/2006 |
| WO | 2006/029385 A2 | 3/2006 |
| WO | 2006-128129 A2 | 11/2006 |
| WO | 2008/008433 A2 | 1/2008 |
| WO | 2008/008433 A3 | 9/2008 |
| WO | 2006/128129 A3 | 10/2008 |
| WO | 2010/006072 A2 | 1/2010 |
| WO | 2011/112635 A1 | 9/2011 |
| WO | 2011/146727 A1 | 11/2011 |
| WO | 2012/066518 A1 | 5/2012 |
| WO | 2013/152342 A1 | 10/2013 |
| WO | 2013/173223 A1 | 11/2013 |
| WO | 2015112888 A1 | 7/2015 |
| WO | 2016/073871 A1 | 5/2016 |
| WO | 2016/073877 A1 | 5/2016 |
| WO | 2016/073884 A1 | 5/2016 |
| WO | 2020009971 A1 | 1/2020 |
| WO | 2021051135 A1 | 3/2021 |

OTHER PUBLICATIONS

Harrison, J.W. et al. (Jul. 2015, e-published Jan. 22, 2015). "Renal Cell Carcinoma Presenting with Paraneoplastic Hallucinations and Cognitive Decline from Limbic Encephalitis." Journal of General Internal Medicine 30(7): 1037-1040.

International Search Report dated Dec. 23, 2015 for International Application No. PCT/US2015/059512, filed Nov. 6, 2015, 4 pages.

Pal, S.K. et al. (Aug. 2014, e-published Jun. 26, 2014). "Adjuvant therapy for renal cell carcinoma: past, present, and future." Oncologist 19(8):851-859.

Philips, GG et al. (Oct. 16, 2014). "Therapeutic Uses of Anti-PD-1 and Anti-PD-L1 Antibodies." International Immunology 27(1):39-46.

Chinese Search Report issued in Chinese Application No. 201580072613.9, dated Dec. 26, 2019, 2 pages.

Chinese Search Report received for Chinese Patent Application No. 201580072608.8, dated Oct. 8, 2019, 4 pages.

Chinese Search Report received for Chinese Patent Application No. 201580072610.5, dated Nov. 4, 2019, 3 pages.

(2018) Definition of stage III melanoma—NCI Dictionary of Cancer Terms—National Cancer Institute, Available at: https://www.cancer.gov/publications/dictionaries/cancer-terms/def/stage-iii-melanoma, 2 pages.

(2018) Definition of stage IV melanoma—NCI Dictionary of Cancer Terms—National Cancer Institute, (https://www.cancer.gov/publications/dictionaries/cancer-terms/def/stage-iv-melanoma) 1 page.

Extended European Search Report for EP Application No. EP15740043.3, dated Sep. 4, 2017, 7 pages.

Extended European Search Report issued in European Application No. 19171060.7, dated Nov. 15, 2019, 4 pages.

International Preliminary Report on Patentability in International Application No. PCT/US2015/012733, dated Jul. 26, 2016, 6 pages.

International Preliminary Report on Patentability received for PCT Application No. CT/US2015/059502, dated May 9, 2017, 07 pages.

International Preliminary Report on Patentability received for PCT Application No. PCT/US2015/059512, dated May 9, 2017, 06 pages.

International Preliminary Report on Patentability received for PCT Application No. PCT/US2015/059526, dated May 9, 2017, 08 pages.

International Search Report for International Application No. PCT/US2015/059502, filed Nov. 6, 2015, dated Dec. 23, 2015, 04 pages.

International Search Report received for PCT Application No. PCT/US2015/059526, dated Dec. 23, 2015, 11 pages.

International Search Report Issued in PCT/US2015/012733, dated Apr. 15, 2015, 9 pages.

Official Office action (English translation) dated Feb. 5, 2019 for Japanese Patent Application No. 2016-548172, filed Jan. 23, 2015, 3 pages.

Russian Search Report issued in Russian Application No. 2017119064, dated Jun. 3, 2019, 4 pages (2 pages of English Translation and 2 pages of Foreign Language).

Russian Search Report issued in Russian Application No. 2017119065, dated Jun. 5, 2019, 4 pages (2 pages of English Translation & 2 pages of Foreign Language).

Russian Search Report issued in Russian Application No. 2017119066, dated Jun. 7, 2019, 4 pages (2 pages of English Translation & 2 pages of Foreign language).

Aapro et al. (Sep. 1, 2006) "A Phase III, Double-Blind, Randomized Trial of Palonosetron Compared with Ondansetron in Preventing Chemotherapy-Induced Nausea and Vomiting Following Highly Emetogenic Chemotherapy", Annals of Oncology, 17(9):1441-1449.

Anestis et al. (Jun. 2018) "Current Advances of Targeting HGF/c-Met Pathway in Gastric Cancer", Annals of Translational Medicine, 6(12):10 pages.

Balla et al. (Jul. 2013) "Phosphoinositides: Tiny Lipids with Giant Impact on Cell Regulation", Physiological Reviews, 93(3):1019-1137.

Bryant et al. (Apr. 2019) "Combination of ERK and Autophagy Inhibition as a Treatment Approach for Pancreatic Cancer", Nature Medicine, 25(4):628-640 (53 pages).

Burakoff et al., (Jul. 2006) "A Phase 1/2a Trial of Sta 5326, an Oral Interleukin-12/23 Inhibitor, in Patients with Active Moderate to Severe Crohn's Disease", Inflammatory Bowel Diseases, 12(7):558-565.

Chong et al. (Jul. 2011) "Cardiovascular Disease and Mtor Signaling", Cardiovascular Medicine, 21(5):151-155.

Chou et al. (1984) "Quantitative Analysis of Dose-Effect Relationships: The Combined Effects of Multiple Drugs or Enzyme Inhibitors", Advances in Enzyme Regulation, 22:27-55.

Choueiri et al. (Nov. 2014) "Pd-l1 Expression in Nonclear-cell Renal Cell Carcinoma", Annals of Oncology, 25(11):2178-2184.

Chougule et al. (Jan. 15, 2008) "Nano-Liposomal Dry Powder Inhaler of Tacrolimus: Preparation, Characterization, and Pulmonary Pharmacokinetics", International Journal of Nanomedicine, 2(4):675-688.

Cross Ryan (Jun. 3, 2019) "Adjusting the Yin and Yang of the Cell", Chemical & Engineering Data, 97(22):35-39.

Dankner et al. (Mar. 15, 2018) "Classifying BRAF Alterations in Cancer: New Rational Therapeutic Strategies for Actionable Mutations", Oncogene, 37(24):3183-3199.

Dibble et al. (Aug. 24, 2012) "TBC1D7 is a Third Subunit of the TSC1-TSC2 Complex Upstream of mTorC1", Molecular Cell, 47(4):535-546.

Dorard et al. (Feb. 15, 2017) "Deciphering the RAS/ERK Pathway in Vivo", Biochemical Society Transactions, 45(1):27-36.

Duvallet et al. (Nov. 2011) "Interleukin-23: A Key Cytokine in Inflammatory Diseases", Annals of Medicine, 43(7):503-511.

Eden et al. (Feb. 2009) "Down-regulation of Epidermal Growth Factor Receptor Signalling Within Multivesicular Bodies", Biochemical Society Transactions, 37(Pt 1):173-177.

Edkins et al. (Aug. 2006) "Recurrent KRAS Codon 146 Mutations in Human Colorectal Cancer", Cancer Biology & Therapy, 5(8):928-932.

Elder et al. (Jul. 2010) "The Utility of Sulfonate Salts in Drug Development", Journal of Pharmaceutical Sciences, 99(7):2948-2961.

Er et al. (Jun. 2013) "AKT Facilitates EGFR Trafficking and Degradation by Phosphorylating and Activating PIKfyve", Science Signaling, ra45, 6(279):13 pages.

(56) References Cited

OTHER PUBLICATIONS

Feldman et al. (Feb. 10, 2009) "Active-site Inhibitors of mTor Target Rapamycin-resistant Outputs of mTORCI and mTORC2", PLoS Biology, e1000038, 7(2):13 pages.
Foster et al. (Apr. 11, 2016) "Activation Mechanism of Oncogenic Deletion Mutations in BRAF, EGFR, and HER2", Cancer Cell, 29(4):477-493.
Frampton et al. (Aug. 2015) "Activation of MET via Diverse Exon 14 Splicing Alterations Occurs in Multiple Tumor Types and Confers Clinical Sensitivity to MET Inhibitors", Cancer Discovery, 5(8):850-859.
Gayle et al. (Apr. 14, 2017) "B-cell Non-Hodgkin Lymphoma: Selective Vulnerability to PIKFYVE Inhibition", Autophagy, 13(6):1082-1083.
Gayle et al. (Mar. 30, 2017) "Identification of Apilimod as a First-in-class PIKfyve Kinase Inhibitor for Treatment of B-cell Non-Hodgkin Lymphoma", Blood, 129(13):1768-1778.
Gomez Manuel R. (1991) "Phenotypes of the Tuberous Sclerosis Complex with a Revision of Diagnostic Criteria", Annals of the New York Academy of Sciences, 615:1-7.
Grothey et al. (Jan. 26, 2013) "Regorafenib Monotherapy for Previously Treated Metastatic Colorectal Cancer (CORRECT): An International, Multicentre, Randomised, Placebo-Controlled, Phase 3 Trial", The Lancet, 381(9863):303-312.
Guo et al. (Mar. 1, 2011) "Activated Ras Requires Autophagy to Maintain Oxidative Metabolism and Tumorigenesis", Genes & Development, 25(5):460-470.
Hobbs et al. (2016) "RAS Isoforms and Mutations in Cancer at a Glance", Journal of Cell Science, 129(7):1287-1292.
Hobbs et al. (Mar. 2016) "Selective Targeting of the KRAS G12C Mutant: Kicking KRAS When It's Down", Cancer Cell, 29(3):251-253.
Howe et al. (Jun. 1995) "Rodent Model of Reproductive Tract Leiomyomata. Establishment and Characterization of Tumor-Derived Cell Lines", The American Journal of Pathology, 146(6):1568-1579.
Hu et al. (Nov. 29, 2018) "Mutational Landscape of Secondary Glioblastoma Guides MET-Targeted Trial in Brain Tumor", Cell, 175(6):1665-1678 (33 pages).
Huang et al. (Jul. 2019) "The HGF-MET Axis Coordinates Liver Cancer Metabolism and Autophagy for Chemotherapeutic Resistance", Autophagy, 15(7):1258-1279.
Inokuchi et al. (Nov. 15, 2015) "Clinical Significance of MET in Gastric Cancer", World Journal of Gastrointestinal Oncology, 7(11):317-327.
Janes et al. (Jan. 25, 2018) "Targeting KRAS Mutant Cancers with a Covalent G12C-Specific Inhibitor", Cell, 172(3):578-589 (30 pages).
Jefferies et al. (Feb. 2008) "A Selective PIKfyve Inhibitor Blocks PtdIns(3,5)P2 Production and Disrupts Endomembrane Transport and Retroviral Budding", EMBO Reports, 9(2):164-170.
Johansson et al. (May 2014) "BRAF Inhibitors in Cancer Therapy", Pharmacology & Therapeutics, 142(2):176-182.
Jordon et al. (2012) "Vemurafenib for the Treatment of Melanoma", Expert Opinion on Pharmacotherapy, 13(17):2533-2543.
Kantola et al. (Nov. 6, 2012) "Stage-Dependent Alterations of the Serum Cytokine Pattern in Colorectal Carcinoma", British Journal of Cancer, 107(10):1729-1736.
Katiyar et al. (Nov. 1, 2007) "Interleukin-12 and Photocarcinogenesis", Toxicology and Applied Pharmacology, 224(3):220-227.
Kholodov et al. (1985) "Klinicheskaya Farmakokinetika", Meditsina, 26 pages.
Kidger et al. (Jul. 2018) "ERK1/2 inhibitors: New weapons to Inhibit the RAS-regulated RAF-MEK1/2-ERK1/2 Pathway", Pharmacology & Therapeutics, 187:45-60.
Kim et al. (Mar. 24, 2017) "Progress of Antibody-based Inhibitors of the HGF-cMET Axis in Cancer Therapy", Experimental & Molecular Medicine, e307, 49(3):7 pages.
Kim et al. (Oct. 1, 2007) "The Phosphoinositide Kinase PIKfyve Mediates Epidermal Growth Factor Receptor Trafficking to the Nucleus", Cancer Research, 67(19):9229-9237.
Kinsey et al. (Apr. 2019) "Protective Autophagy Elicited by RAF→MEK→ERK Inhibition Suggests a Treatment Strategy for RAS-driven Cancers", Nature Medicine, 25(4):620-627 (27 pages).
Krausz et al. (May 25, 2012) "A Phase IIa, Randomized, Double-Blind, Placebo-Controlled Trial of Apilimod Mesylate, an Interleukin-12/Interleukin-23 Inhibitor, in Patients with Rheumatoid Arthritis", Arthritis and Rheumatism, 64(6):1750-1755.
Labiris et al. (Dec. 2003) "Pulmonary Drug Delivery. Part II: The Role of Inhalant Delivery Devices and Drug Formulations in Therapeutic Effectiveness of Aerosolized Medications", British Journal of Clinical Pharmacology, 56(6):600-612.
Lan et al. (May 6, 2011) "IL-23/IL-23R: Potential Mediator of Intestinal Tumor Progression from Adenomatous Polyps to Colorectal Carcinoma", International Journal of Colorectal Disease, 26(12):1511-1518.
Langowski et al. (Jul. 27, 2006) "IL-23 Promotes Tumour Incidence and Growth", Nature, 442(7101):461-465.
Laplante et al. (2009) "mTor Signaling at a Glance", Journal of Cell Science, 3589-3594.
Laplante et al. (Apr. 13, 2012) "mTOR Signaling in Growth Control and Disease", Cell, 149(2):274-293.
Lee et al. (Mar. 5, 2019) "MAP Kinase and Autophagy Pathways Cooperate to Maintain RAS Mutant Cancer Cell Survival", Proceedings of the National Academy of Sciences of the United States of America, 116(10):4508-4517.
Lin et al. (Feb. 2019) "Targeting Autophagy Potentiates Antitumor Activity of Met-TKIs Against Met-amplified Gastric Cancer", Cell Death & Disease, 10(2):11 pages.
Liu et al. (2009) "mTOR Mediated Anti-Cancer Drug Discovery", Drug Discovery Today Therapeutic Strategies, 6(2):14 pages.
Martin et al. (Mar. 27, 2013) "Inhibition of PIKfyve by YM-201636 Dysregulates Autophagy and Leads to Apoptosis-Independent Neuronal Cell Death", PLoS One, e60152, 8(3):14 pages.
Masliah-Planchon et al. (Jun. 21, 2016) "RAS-MAPK Pathway Epigenetic Activation in Cancer: miRNAs in Action", Oncotarget, 7(25):38892-38907.
Menon et al. (2009) "Common Corruption of the mTor Signaling Network in Human Tumors", Oncogene, 27:S43-S51.
Michaelis et al. (Apr. 26, 2012) "Dabigatran and Dabigatran Ethyl Ester: Potent Inhibitors of Ribosyldihydronicotinamide Dehydrogenase (NQO2)", Journal of Medicinal Chemistry, 55(8):3934-3944.
Miranda et al. (Sep. 2018) "Status of Agents Targeting the HGF/c-Met Axis in Lung Cancer", Cancers, 10(9):18 pages.
Mo et al. (Sep. 2017) "Targeting MET in cancer Therapy", Chronic Diseases and Translational Medicine, 3(3):148-153.
NANZANDO (Jan. 16, 1998) "Dictionary of Medicine", 18th Edition, 13-14, 261 pages.
Ni et al. (Oct. 2019) "Drugging K-RasG12C through Covalent Inhibitors: Mission Possible?", Pharmacology & Therapeutics, 202:49 pages.
Novero et al. (2014) "Ibrutinib for B cell malignancies", Experimental Hematology & Oncology, 3(4):7 pages.
Onda et al. (Sep. 1999) "Tsc2(+/−) Mice Develop Tumors in Multiple Sites that Express Gelsolin and are Influenced by Genetic Background", Journal of Clinical Investigation, 104(6):687-695.
Pal et al., (Aug. 2013) "Adjuvant Therapy in Renal Cell Carcinoma—Past, Present, and Future", Seminars in Oncology, 40(4):482-491.
Palanisamy et al. (Jul. 2010) "Rearrangements of the RAF Kinase Pathway in Prostate Cancer, Gastric Cancer and Melanoma", Nature Medicine, 16(7):793-798 (13 pages).
Pant et al. (Oct. 2018) "Clinical Update on K-Ras Targeted Therapy in Gastrointestinal Cancers", Critical Reviews in Oncology/Hematology, 130:78-91 (36 pages).
Pilotto et al. (Jan. 2017) "MET Exon 14 Juxtamembrane Splicing Mutations: Clinical and Therapeutical Perspectives for Cancer Therapy", Annals of Translational Medicine, 5(1):11 pages.
Puls et al. (2011) "Current Status of Src Inhibitors in Solid Tumor Malignancies", The Oncologist, 16(5):566-578.
Rehman et al. (Mar. 2019) "MET Inhibition in Non-Small Cell Lung Cancer", European Medical Journal, 6(1):100-111.

(56) References Cited

OTHER PUBLICATIONS

Ritz et al. (Dec. 30, 2015) "Dose-Response Analysis Using R", PLoS One, e0146021, 10(12):13 pages.
Ryan et al. (Nov. 1, 2015) "Targeting RAS-mutant Cancers: is ERK the Key?", Trends Cancer, 1(3):183-198 (26 pages).
Sakano Teruo (May 1991) "Chemotherapy of Malignant Lymphoma, with Special Regard to Non-Hodgkin's Lymphomas", International Journal of Hematology, 32(5):453-460 (11 pages).
Sands et al. (Jul. 2010) "Randomized, Double-Blind, Placebo-Controlled Trial of the Oral Interleukin-12/23 Inhibitor Apilimod Mesylate for Treatment of Active Crohn's Disease", Inflammatory bowel disease, 16(7):1209-1218.
Sergeev (1975) "A Short Course in Molecular Pharmacology", 1 page.
Seton-Rogers et al. (Apr. 1, 2019) "Eliminating Protective Autophagy in KRAS-mutant Cancers", Nature Reviews Cancer, 19:1 page.
Sharma et al. (Oct. 2015) "A Family of PIKFYVE Inhibitors with Therapeutic Potential Against Autophagy-Dependent Cancer Cells Disrupt Multiple Events in Lysosome Homeostasis", Autophagy, 15(10):1694-1718.
STEADMAN (Feb. 20, 2002) "English-Japanese Medical Dictionary", 5th Edition, 3 pages.
Stephens et al. (2017) "Tumor RAS Gene Expression Levels Are Influenced by the Mutational Status of RAS Genes and Both Upstream and Downstream RAS Pathway Genes", Cancer Informatics, 16:1-10.
Tovar et al. (May 2017) "MET in Human Cancer: Germline and Somatic Mutations", Annals of Translational Medicine, 5(10):205-210.
Vengerovskiy (2003) "Pharmacological Incompatibility/ Bulletin of Siberian Medicine", 3:49-56.
Wada et al. (Apr. 6, 2012) "Apilimod Inhibits the Production of IL-12 and IL-23 and Reduces Dendritic Cell Infiltration in Psoriasis", PLOS One, e35069, 7(4):1-10.
Wada et al. (Oct. 19, 2006) "Selective Abrogation of Th1 Response by STA-5326, a Potent IL-12/IL-23 Inhibitor", Blood, 109(3):1156-1164.
Wang et al. (Dec. 19, 2012) "Implications of anti-cytokine therapy in colorectal cancer and autoimmune diseases", Annals of the Rheumatic Diseases, 72(Suppl 2):ii100-ii103.
White Eileen (Mar. 5, 2019) "Blockade of RAF and Autophagy is the One-two Punch to Take Out Ras", Proceedings of the National Academy of Sciences of the United States of America, 116(10):3965-3967.
Wolff et al. (1996) "Metabolic Considerations in Prodrug Design", Burger's Medicinal Chemistry and Drug Discovery. 5th edition, 1:949-982.
Wong Michael (Mar.-Apr. 2013) "Mammalian Target of Rapamycin (mTor) Pathways in Neurological Diseases", Biomedical Journal, 36(2):40-50.
Yaeger et al. (Mar. 2019) "Targeting Alterations in the RAF-MEK Pathway", Cancer Discovery, 9(3):329-341.
Young et al. (Jul. 1998) "The Genetic Basis of Tuberous Sclerosis", Molecular Medicine Today, 4(7):313-319.
Zhang et al. (Oct. 2003) "Loss of Tsc1/Tsc2 Activates mTOR and Disrupts PI3K-Akt Signaling Through Downregulation of PDGFR", Journal of Clinical Investigation, 112(8):1223-1233.
Zhang et al. (Apr. 2016) "Regulation of the MET Oncogene: Molecular Mechanisms", Carcinogenesis, 37(4):345-355.
International Search Report and Written Opinion received for PCT Application No. PCT/US20/70522, dated Nov. 25, 2020, 13 pages.
Kim et al. (Nov. 2016) "Targeting Cancer Metabolism by Simultaneously Disrupting Parallel Nutrient Access Pathways", The Journal of Clinical Investigation, 126(11):4088-4102.
Krishna et al. (Sep. 12, 2016) "PIKfyve Regulates Vacuole Maturation and Nutrient Recovery following Engulfment", Development Cell, 38(5):536-547.

* cited by examiner

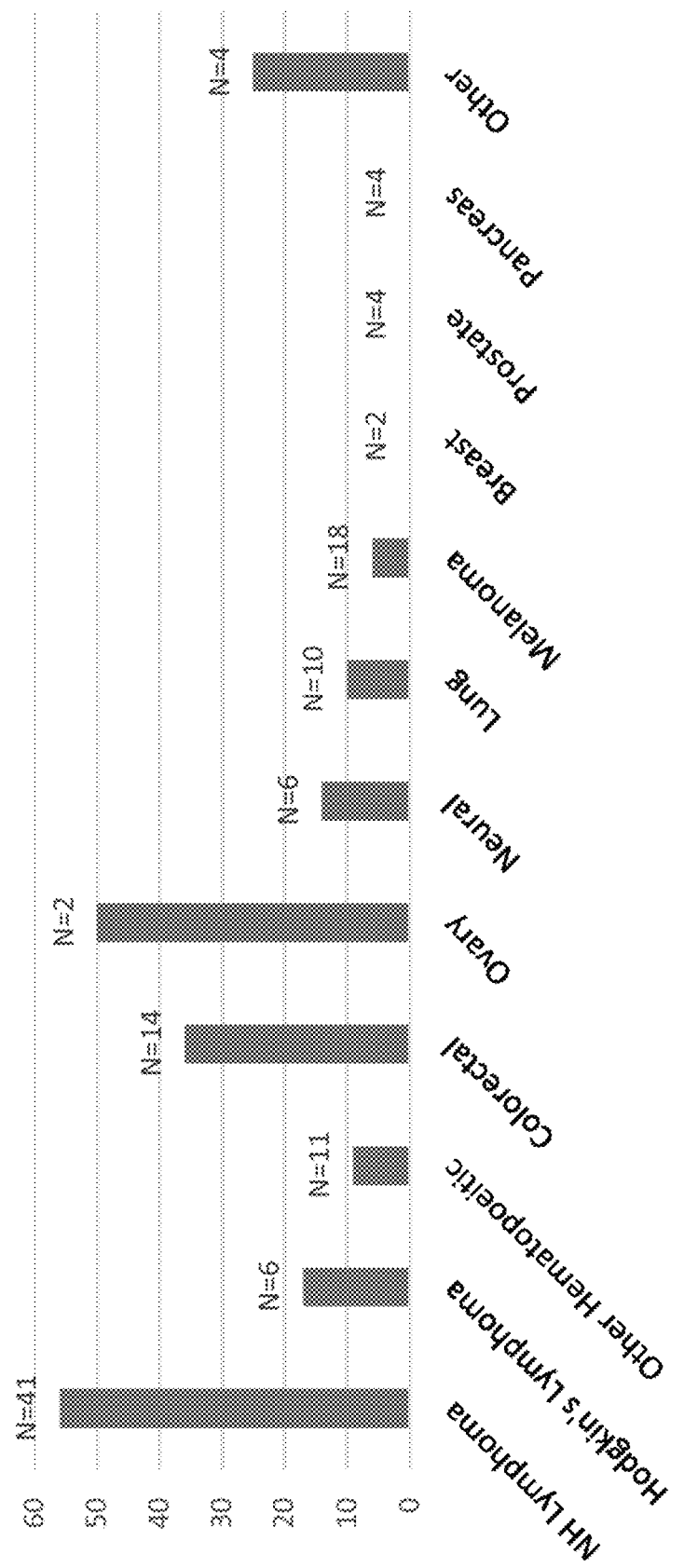

APILIMOD COMPOSITIONS AND METHODS FOR USING SAME IN THE TREATMENT OF RENAL CANCER

RELATED APPLICATIONS

This application is a continuation application of U.S. Ser. No. 16/226,175, filed Dec. 19, 2018, now abandoned, which is a continuation of U.S. Ser. No. 15/524,884, filed May 5, 2017, now U.S. Pat. No. 10,206,910 issued Feb. 19, 2019, which is a national stage entry, filed under 35 U.S.C. § 371, of International Application No. PCT/US2015/059512, filed on Nov. 6, 2015, which claims priority to U.S. Ser. No. 62/077,127, filed on Nov. 7, 2014, the contents of which are hereby fully incorporated by reference.

FIELD OF THE DISCLOSURE

The present disclosure relates to compositions comprising apilimod and methods of using same for the treatment of renal cancer.

BACKGROUND OF THE DISCLOSURE

Apilimod, also referred to as STA-5326, hereinafter "apilimod", is recognized as a potent transcriptional inhibitor of IL-12 and IL-23. See e.g., Wada et al. *Blood* 109 (2007): 1156-1164. IL-12 and IL-23 are inflammatory cytokines normally produced by immune cells, such as B-cells and macrophages, in response to antigenic stimulation. Autoimmune disorders and other disorders characterized by chronic inflammation are characterized in part by inappropriate production of these cytokines. In immune cells, the selective inhibition of IL-12/IL-23 transcription by apilimod was recently shown to be mediated by apilimod's direct binding to phosphatidylinositol-3-phosphate 5-kinase (PIKfyve). See, e.g., Cai et al. *Chemistry and Biol.* 20 (2013):912-921. PIKfyve plays a role in Toll-like receptor signaling, which is important in innate immunity.

Based upon its activity as an immunomodulatory agent and a specific inhibitor of IL-12/IL-23, apilimod has been proposed as useful in treating autoimmune and inflammatory diseases and disorders. See e.g., U.S. Pat. Nos. 6,858,606 and 6,660,733 (describing a family of pyrimidine compounds, including apilimod, purportedly useful for treating diseases and disorders characterized by IL-12 or IL-23 overproduction, such as rheumatoid arthritis, sepsis, Crohn's disease, multiple sclerosis, psoriasis, or insulin dependent diabetes mellitus). Similarly, apilimod was suggested to be useful for treating certain cancers based upon its activity to inhibit c-Rel or IL-12/23, particularly in cancers where these cytokines were believed to play a role in promoting aberrant cell proliferation role. See e.g., WO 2006/128129 and Baird et al., *Frontiers in Oncology* 3:1 (2013, respectively).

Each of three clinical trials of apilimod has focused on its potential efficacy in autoimmune and inflammatory diseases. The trials were conducted in patients having psoriasis, rheumatoid arthritis, and Crohn's disease. An open label clinical study in patients with psoriasis concluded that oral administration of apilimod showed immunomodulatory activity supporting the inhibition of IL-12/IL-23 synthesis for the treatment of TH1- and TH17-mediated inflammatory diseases. Wada et al., *PLosOne* 7:e35069 (April 2012). But the results of controlled trials in rheumatoid arthritis and Crohn's disease did not support the notion that IL-12/IL-23 inhibition by apilimod translates into clinical improvement in either of these indications. In a randomized, double-blind, placebo-controlled Phase II clinical trial of apilimod in patients with rheumatoid arthritis, apilimod failed to alter synovial IL-12 and IL-23 expression. Krauz et al., *Arthritis & Rheumatism* 64:1750-1755 (2012). The authors concluded that the "results do not support the notion the IL-12/IL-23 inhibition by apilimod is able to induce robust clinical improvement in RA." Similarly, a randomized, double-blind, placebo-controlled trial of apilimod for treatment of active Crohn's disease concluded that, although well tolerated, apilimod did not demonstrate efficacy over placebo. Sands et al *Inflamm Bowel Dis.* 2010 July; 16(7): 1209-18.

The mammalian target of rapamycin (mTOR) pathway is an important cellular signaling pathway that is involved in multiple physiological functions, including cell growth, cell proliferation, metabolism, protein synthesis, and autophagy (La Plante et al *Cell* 2012, (149 (2), pp. 274-293). mTOR is a kinase that integrates intracellular and extracellular cues that signal the levels of amino acids, stress, oxygen, energy, and growth factors and regulates the cellular response to these environment cues. mTOR deregulation has been implicated in a wide range of disorders and diseases, including cancer, obesity, diabetes, and neurodegeneration. Certain components of the mTOR pathway have been explored as drug targets for treating some of these diseases. However, therapeutic efficacy has been limited, for example, in the treatment of some cancers, and some mTOR inhibitors have been shown to have an adverse effect on metabolism. The tuberous sclerosis complex tumor suppressor genes, TSC1 and TSC2, are negative regulators of mTOR.

SUMMARY OF THE DISCLOSURE

The present disclosure is based in part on the surprising discovery that apilimod is a highly cytotoxic agent in TSC null cells. In these cells, the mTOR pathway is constitutively active. The mTOR pathway is activated in a number of cancers, and in further screening of over 100 cancer cell lines apilimod showed anti-proliferative activity in cell lines from diverse cancers, including renal cell carcinomas. Furthermore, the cytotoxic activity of apilimod in cancer cell lines was due to an inhibition of intracellular trafficking and a corresponding increase in apoptosis and/or autophagy, rather than via apilimod's inhibition of IL-12/23 production, as would have been predicated based upon apilimod's immunomodulatory activity. In addition, a screen over 450 kinases identified PIKfyve as the only high affinity binding target (Kd=75 pM) for apilimod. The present disclosure provides new methods for the therapeutic use of apilimod in treating cancer renal cell cancer.

In one aspect, the disclosure provides a composition for treating renal cancer in a subject having renal cancer, the composition comprising a therapeutically effective amount of apilimod, or a pharmaceutically acceptable salt thereof. In embodiments, the apilimod is apilimod dimesylate. In embodiments, the composition is in a form suitable for oral or intravenous administration. In embodiments, the composition further comprises at least one additional active agent, which may be selected from a therapeutic agent or a non-therapeutic agent, or a combination of a therapeutic agent and a non-therapeutic agent. In embodiments, the at least one additional active agent is a therapeutic agent selected from the group consisting of a protein kinase inhibitor, a platinum based anti-neoplastic agent, a topoisomerase inhibitor, a nucleoside metabolic inhibitor, an alkylating agent, an intercalating agent, a tubulin binding agent, and combinations thereof. In embodiments, the therapeutic agent is a protein kinase inhibitor. In embodiments, the protein kinase inhibitor is pazopanib or sorafenib, or a combination thereof. The composition may further comprise a non-therapeutic agent selected to ameliorate one or more side effects of the apilimod. In embodiments, the non-therapeutic agent is selected from the group consisting of ondanestron, granisetron, dolsetron, and palonosetron. In embodiments, the non-therapeutic agent is selected from the group consisting of pindolol and risperidone.

In embodiments, the composition comprises an amount of the apilimod dimesylate effective to inhibit PIKfyve kinase activity in the cancer cells of the subject. The renal cancer may in some embodiments be refractory to standard treatment or metastatic. In embodiments, the renal cancer is selected from clear cell renal carcinoma, a transitional cell carcinoma, Wilms tumor (nephroblastoma), renal sarcoma, and benign (non-cancerous) kidney tumors, renal adenoma, oncocytoma, and angiomyolipoma.

In one aspect, the disclosure provides a method for treating renal cancer in a subject in need thereof, the method comprising administering to the subject a therapeutically effective amount of apilimod, or a composition comprising apilimod, wherein the apilimod is apilimod itself (i.e., apilimod free base), or a pharmaceutically acceptable salt, solvate, clathrate, hydrate, polymorph, prodrug, analog or derivative thereof. In one embodiment, the apilimod is apilimod free base or apilimod dimesylate.

In embodiments, the method further comprises administering at least one additional active agent to the subject. The at least one additional active agent may be a therapeutic agent or a non-therapeutic agent. The at least one additional active agent may be administered in a single dosage form with the apilimod, or in a separate dosage form from the apilimod. In embodiments, the at least one additional active agent is a therapeutic agent selected from the group consisting of a protein kinase inhibitor, a platinum based antineoplastic agent, a topoisomerase inhibitor, a nucleoside metabolic inhibitor, an alkylating agent, an intercalating agent, a tubulin binding agent, PD-1/PDL-1 pathway inhibitor, and combinations thereof. In embodiments, the therapeutic agent is a protein kinase inhibitor. In embodiments, the protein kinase inhibitor is pazopanib or sorafenib, or a combination thereof. In embodiments, the at least one additional active agent is a therapeutic agent selected from the group consisting of sorafenib (Nexavar®), sunitinib (Sutent®) temsirolimus (Torisel®), everolimus (Afinitor®), bevacizumab (Avastin®), pazopanib (Votrient®), axitinib (Inlya®) and combinations thereof. In embodiments, the therapeutic agent is a PD-1/PDL-1 pathway inhibitor. In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In embodiments, the at least one active agent is a non-therapeutic agent selected to ameliorate one or more side effects of apilimod. In embodiments, the non-therapeutic agent is selected from the group consisting of ondanestron, granisetron, dolsetron, and palonosetron. In one embodiment, the non-therapeutic agent is selected from the group consisting of pindolol and risperidone. In one embodiment, the dosage form of the apilimod composition is an oral dosage form. In another embodiment, the dosage form of the apilimod composition is suitable for intravenous administration, administration is by a single injection or by a drip bag.

In one embodiment, the subject is a human cancer patient. In one embodiment, the human cancer patient in need of treatment with apilimod is on whose cancer is refractory to a standard chemotherapy regimen. In one embodiment, the human cancer patient in need of the treatment with apilimod is one whose cancer as recurred following treatment with a standard chemotherapy regimen. In one embodiment, the cancer is a renal cancer. In one embodiment, the renal cancer is a transitional cell carcinoma, Wilms tumor (nephroblastoma), renal sarcoma, and benign (non-cancerous) kidney tumors, renal adenoma, oncocytoma, and angiomyolipoma. In one embodiment, the renal cancer is a clear cell renal cell carcinoma.

In one embodiment, the standard chemotherapy regimen comprises one or more therapeutic agents selected from the group consisting of ibrutinib, rituximab, doxorubicin, prednisolone, vincristine, velcade, cycloposphoamide, dexamethasone and everolimus.

In one embodiment, the method is a method for treating renal cancer using a combination therapy comprising apilimod and a chemotherapy regimen for the treatment of the renal cancer. In embodiments, the chemotherapy regimen comprises a PD-1/PDL-1 pathway inhibitor. In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In another embodiment, the method is a method for treating renal cancer using a combination therapy comprising apilimod and an immunotherapy regimen for the treatment of the renal cancer. In one embodiment the immunotherapy regime is the Interleukin-2 (IL-2) regime or the alpha-interferon regime. In one embodiment, the immunotherapy regimen comprises a PD-1/PDL-1 pathway inhibitor. In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In some embodiments, the method is a method for treating renal cancer using a combination therapy comprising apilimod and a protein kinase inhibitor regimen for the treatment of the renal cancer. In one embodiment the protein kinase inhibitor regimen is sorafenib, sunitinib, bevacizumab, lenvatinib, everolimus.

BRIEF DESCRIPTION OF THE DRAWINGS

FIGS. 2A-B: A, percentage of cell lines with IC50 less than 500 nM; B, normal lung fibroblasts are not sensitive to apilimod-induced cytotoxicity at apilimod concentrations as high as 10 micromolar.

DETAILED DESCRIPTION OF THE DISCLOSURE

Figure 1:
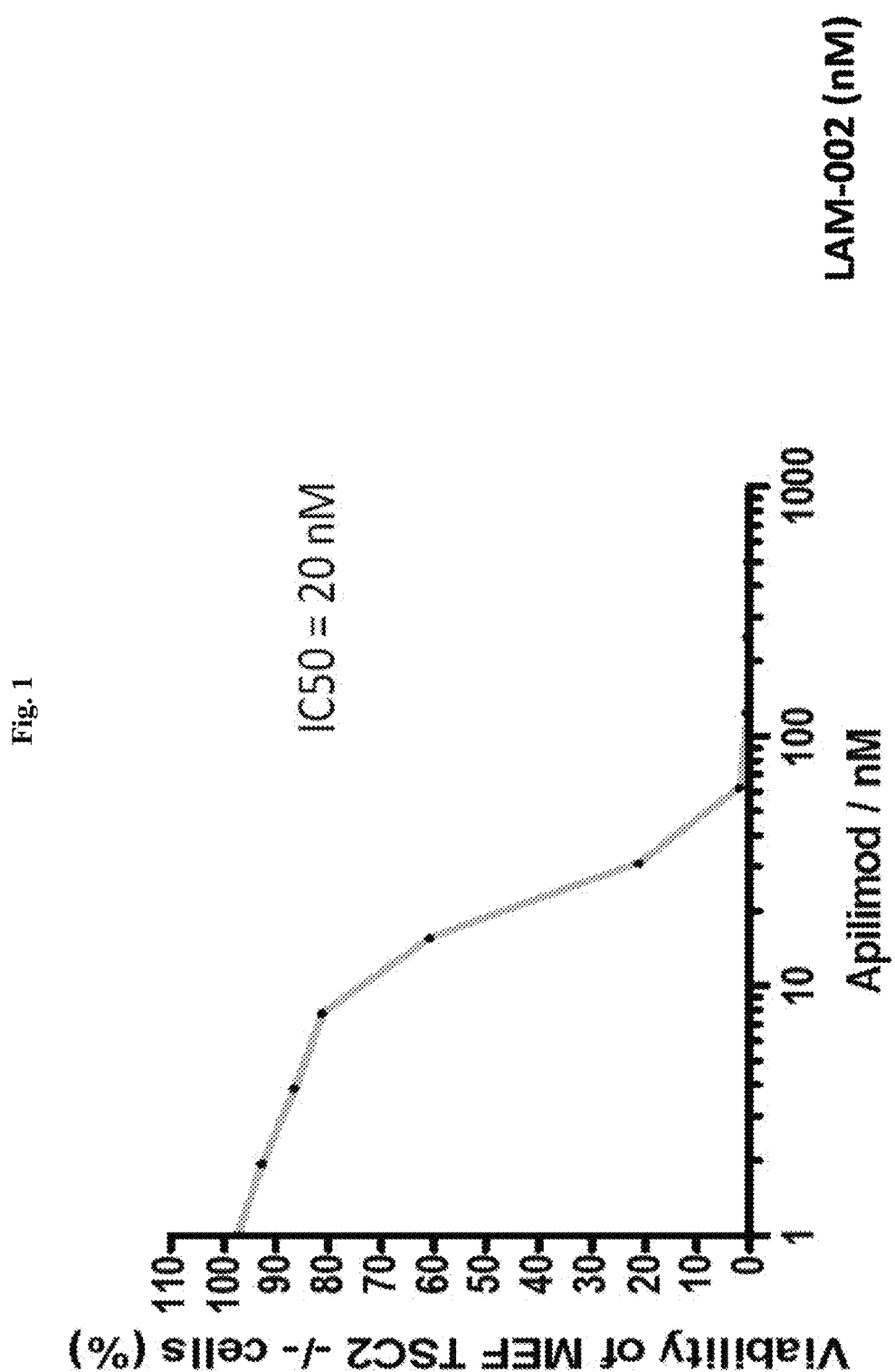
FIG. 1: TSC2 deficient cells are highly sensitive to apilimod ($IC_{50}$=20 nM).

The present disclosure provides compositions and methods related to the use of apilimod for treating renal cancer in a subject, preferably a human subject, in need of such treatment. The present disclosure generally relates to new uses of apilimod based upon the surprising discovery of apilimod's cytotoxic activity against a range of cancer cells of both lymphoid and non-lymphoid origin, an activity that is not clearly related to, or predictable from, apilimod's known immunomodulatory and IL-12/23 inhibitory activity.

In addition, the present disclosure provides novel therapeutic approaches to cancer treatment based upon combination therapy utilizing apilimod and at least one additional therapeutic agent. The combination therapies described herein exploit the unique cytotoxic activity of apilimod which is shown to provide a synergistic effect when combined with other anti-cancer agents.

As used herein, the term "apilimod" may refer to apilimod itself (i.e., apilimod free base), or may encompass pharmaceutically acceptable salts, solvates, clathrates, hydrates, polymorphs, metabolites, prodrugs, analogs or derivatives of apilimod, as described below. The structure of apilimod is shown in Formula I:

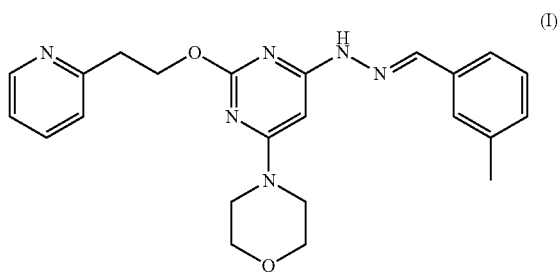 [SMILES: Cc1cccc(/C=N/Nc2cc(N3CCOCC3)nc(OCCc3ccccn3)n2)c1]

The chemical name of apilimod is 2-[2-Pyridin-2-yl)-ethoxyl-4-N'-(3-methyl-benzilidene)-hydrazino]-6-(morpholin-4-yl)-pyrimidine (IUPAC name: (E)-4-(6-(2-(3-methylbenzylidene)hydrazinyl)-2-(2-(pyridin-2-yl)ethoxy) pyrimidin-4-yl)morpholine), and the CAS number is 541550-19-0.

Apilimod can be prepared, for example, according to the methods described in U.S. Pat. Nos. 7,923,557, and 7,863,270, and WO 2006/128129.

As used herein, the term "pharmaceutically acceptable salt," is a salt formed from, for example, an acid and a basic group of apilimod. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts.

The term "pharmaceutically acceptable salt" also refers to a salt prepared from an apilimod composition having an acidic functional group, such as a carboxylic acid functional group, and a pharmaceutically acceptable inorganic or organic base.

The term "pharmaceutically acceptable salt" also refers to a salt prepared from apilimod having a basic functional group, such as an amino functional group, and a pharmaceutically acceptable inorganic or organic acid.

The salts of the compounds described herein can be synthesized from the parent compound by conventional chemical methods such as methods described in Pharmaceutical Salts: Properties, Selection, and Use, P. Hemrich Stalil (Editor), Camille G. Wermuth (Editor), ISBN: 3-90639-026-8, August 2002. Generally, such salts can be prepared by reacting the parent compound (e.g., 2-[2-Pyridin-2-yl)-ethoxyl-4-N'-(3-methyl-benzilidene)-hydrazino]-6-(morpholin-4-yl)-pyrimidine) with the appropriate acid in water or in an organic solvent, or in a mixture of the two.

One salt form of a compound described herein can be converted to the free base and optionally to another salt form by methods well known to the skilled person. For example, the free base can be formed by passing the salt solution through a column containing an amine stationary phase (e.g. a Strata-NH$_2$ column). Alternatively, a solution of the salt in water can be treated with sodium bicarbonate to decompose the salt and precipitate out the free base. The free base may then be combined with another acid using routine methods.

As used herein, the term "polymorph" means solid crystalline forms of a compound of the present disclosure (e.g., 2-[2-Pyridin-2-yl)-ethoxyl-4-N'-(3-methyl-benzilidene)-hydrazino]-6-(morpholin-4-yl)-pyrimidine) or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present disclosure (e.g., 2-[2-Pyridin-2-yl)-ethoxyl-4-N'-(3-methyl-benzilidene)-hydrazino]-6-(morpholin-4-yl)-pyrimidine) or a salt thereof, which further includes a stoichiometric or non-stoichiometric amount of water bound by non-covalent intermolecular forces.

As used herein, the term "clathrate" means a compound of the present disclosure (e.g., 2-[2-Pyridin-2-yl)-ethoxyl-4-N'-(3-methyl-benzilidene)-hydrazino]-6-(morpholin-4-yl)-pyrimidine) or a salt thereof in the form of a crystal lattice that contains spaces (e.g., channels) that have a guest molecule (e.g., a solvent or water) trapped within.

As used herein, the term "prodrug" means a derivative of a compound described herein (e.g., 2-[2-Pyridin-2-yl)-ethoxyl-4-N'-(3-methyl-benzilidene)-hydrazino]-6-(morpholin-4-yl)-pyrimidine) that can hydrolyze, oxidize, or otherwise react under biological conditions (in vitro or in vivo) to provide a compound of the disclosure. Prodrugs may only become active upon such reaction under biological conditions, or they may have activity in their unreacted forms. Examples of prodrugs contemplated in this disclosure include, but are not limited to, analogs or derivatives of a compound described herein (e.g., 2-[2-Pyridin-2-yl)-ethoxyl-4-N'-(3-methyl-benzilidene)-hydrazino]-6-(morpholin-4-yl)-pyrimidine) that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

As used herein, the term "solvate" or "pharmaceutically acceptable solvate," is a solvate formed from the association of one or more solvent molecules to one of the compounds disclosed herein (e.g., 2-[2-Pyridin-2-yl)-ethoxyl-4-N'-(3-methyl-benzilidene)-hydrazino]-6-(morpholin-4-yl)-pyrimidine). The term solvate includes hydrates (e.g., hemi-hydrate, mono-hydrate, dihydrate, trihydrate, tetrahydrate, and the like).

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Methods of Treatment

The present disclosure provides methods for the treatment of renal cancer in a subject in need thereof by administering to the subject a therapeutically effective amount of apilimod, or a pharmaceutically acceptable salt, solvate, clathrate, hydrate, polymorph, prodrug, analog or derivative thereof.

In one embodiment the renal cancer is a renal cell carcinoma (RCC). In one embodiment, the renal cell carcinoma is selected from the group consisting of clear cell renal cell carcinoma, papillary renal cell carcinoma, chromophobe renal cell carcinoma, other rare types of renal cell carcinoma (e.g., Collecting duct RCC, multilocular cystic RCC, medullary carcinoma, mucinous tubular and spindle cell carcinoma, neuroblastoma-associated RCC, unclassified renal cell carcinoma), and metastatic RCC. In one embodiment the renal cancer is selected from the group consisting of transitional cell carcinoma, Wilms tumor (nephroblastoma), renal sarcoma, and benign (non-cancerous) kidney tumors, renal adenoma, oncocytoma, and angiomyolipoma.

The present disclosure also provides methods comprising combination therapy for the treatment of cancer. As used herein, "combination therapy" or "co-therapy" includes the administration of a therapeutically effective amount of apilimod as part of a specific treatment regimen intended to provide the beneficial effect from the co-action of the apilimod and the additional active agent. The at least one additional agent may be a therapeutic agent or a non-therapeutic agent. The beneficial effect of the combination includes, but is not limited to, pharmacokinetic or pharmacodynamic co-action resulting from the combination of therapeutic compounds. The beneficial effect of the combination may also relate to the mitigation of a toxicity, side effect, or adverse event associated with another agent in the combination. "Combination therapy" is not intended to encompass the administration of two or more of these therapeutic compounds as part of separate monotherapy regimens that incidentally and arbitrarily result in a beneficial effect that was not intended or predicted.

The at least one additional active agent may be a therapeutic agent, for example an anti-cancer agent or a cancer chemotherapeutic agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to nontherapeutic agents, the beneficial effect of the combination may relate to the mitigation of a toxicity, side effect, or adverse event associated with a therapeutically active agent in the combination.

In one embodiment, the at least one additional agent is a non-therapeutic agent which mitigates one or more side effects of an apilimod composition, the one or more side effects selected from any of nausea, vomiting, headache, dizziness, lightheadedness, drowsiness and stress. In one aspect of this embodiment, the non-therapeutic agent is an antagonist of a serotonin receptor, also known as 5-hydroxytryptamine receptors or 5-HT receptors. In one aspect, the non-therapeutic agent is an antagonist of a 5-HT3 or 5-HT1a receptor. In one aspect, the non-therapeutic agent is selected from the group consisting of ondansetron, granisetron, dolasetron and palonosetron. In another aspect, the non-therapeutic agent is selected from the group consisting of pindolol and risperidone.

In one embodiment, the at least one additional agent is a therapeutic agent. In one embodiment, the therapeutic agent is an anti-cancer agent as described in more detail below under 'combination therapy'.

In the context of combination therapy, administration of apilimod, or a pharmaceutically acceptable salt, solvate, clathrate, hydrate, polymorph, metabolite, prodrug, analog or derivative thereof, may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The one or more additional active agents can be formulated for co-administration with apilimod in a single dosage form, as described in greater detail herein. The one or more additional active agents can be administered separately from the dosage form that comprises the apilimod. When the additional active agent is administered separately from the apilimod, it can be by the same or a different route of administration as the apilimod.

Preferably, the administration of a composition comprising apilimod in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present disclosure in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

The non-drug treatment can be selected from chemotherapy, radiation therapy, hormonal therapy, anti-estrogen therapy, gene therapy, surgery (e.g. radical nephrectomy, partial nephrectomy, laparoscopic and robotic surgery), radiofrequency ablation, and cryoablation. For example, a non-drug therapy is the removal of an ovary (e.g., to reduce the level of estrogen in the body), thoracentesis (e.g., to remove fluid from the chest), paracentesis (e.g., to remove fluid from the abdomen), surgery to remove or shrink angiomyolipomas, lung transplantation (and optionally with an antibiotic to prevent infection due to transplantation), or oxygen therapy (e.g., through a nasal cannula containing two small plastic tubes or prongs that are placed in both nostrils, through a face mask that fits over the nose and mouth, or through a small tube inserted into the windpipe through the front of the neck, also called transtracheal oxygen therapy).

In one embodiment, the at least one additional agent is an agent which mitigates one or more side effects of apilimod selected from any of nausea, vomiting, headache, dizziness, lightheadedness, drowsiness and stress. In one aspect of this embodiment, the additional agent is an antagonist of a serotonin receptors, also known as 5-hydroxytryptamine receptors or 5-HT receptors. In one aspect, the additional agent is an antagonist of a $5\text{-HT}_3$ or $5\text{-HT}_{1a}$ receptor. In one aspect, the agent is selected from the group consisting of ondansetron, granisetron, dolasetron and palonosetron. In another aspect, the agent is selected from the group consisting of pindolol and risperidone.

In one embodiment, the at least one additional agent is an anti-cancer agent. In one embodiment, the anti-cancer agent is selected from taxol, vincristine, doxorubicin, temsirolimus, carboplatin, ofatumumab, rituximab, and combinations thereof.

In one embodiment, the at least one additional agent is selected from chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In one embodiment, the at least one additional agent is selected from Afinitor (Everolimus), Aldesleukin, Avastin (Bevacizumab), Axitinib, Bevacizumab, Everolimus, IL-2 (Aldesleukin), Inlyta (Axitinib), Interleukin-2 (Aldesleukin), Nexavar (Sorafenib Tosylate), Pazopanib, Hydrochloride, Proleukin (Aldesleukin), Sorafenib Tosylate, Sunitinib Malate, Sutent (Sunitinib Malate), Temsirolimus, Torisel (Temsirolimus), Votrient (Pazopanib Hydrochloride), or combination thereof.

In one embodiment, the at least one additional agent is directed towards targeted therapy, wherein the treatment targets the cancer's specific genes, proteins, or the tissue environment that contributes to cancer growth and survival. This type of treatment blocks the growth and spread of cancer cells while limiting damage to healthy cells.

In one embodiment, the at least one additional agent is directed towards anti-angiogenesis therapy, wherein the treatment focuses on stopping angiogenesis, which is the process of making new blood vessels. Because a tumor needs the nutrients delivered by blood vessels to grow and spread, the goal of anti-angiogenesis therapies is to "starve" the tumor. One anti-angiogenic drug, bevacizumab (Avastin), has been shown to slow tumor growth for people with metastatic renal carcinoma. Bevacizumab combined with interferon slows tumor growth and spread.

In one embodiment, the at least one additional agent is directed towards immunotherapy, also called biologic therapy, is designed to boost the body's natural defenses to fight cancer. It uses materials made either by the body or in a laboratory to improve, target, or restore immune system function. For example, Interleukin-2 (IL-2) is a drug that has been used to treat kidney cancer as well as AM0010, and interleukin-15. They are cellular hormones called cytokines produced by white blood cells and are important in immune system function, including the destruction of tumor cells. Alpha-interferon is another type of immunotherapy used to treat kidney cancer that has spread. Interferon appears to change the proteins on the surface of cancer cells and slow their growth. Many combination therapies of IL-2 and alpha-interferon for patients with advanced kidney cancer combined with chemotherapy are more effective than IL-2 or interferon alone.

In embodiments, the at least one additional agent is a PD-1/PDL-1 pathway inhibitor. In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

Another example is a compound called a check point inhibitor. Treatment with these compounds work by targeting molecules that serve as checks and balances on immune responses. By blocking these inhibitory molecules or, alternatively, activating stimulatory molecules, these treatments are designed to unleash or enhance pre-existing anti-cancer immune responses. Various antibodies include PD-1, anti-CD27, B7-H3, KIR, LAG-3, 4-1BB/CD137, and GITR. Exemplary agents include pembrolizumab (Keytruda, MK-3475, a PD-1 antibody), MPDL3280A (a PD-L1 antibody), varlilumab (CDX-1127, an anti-CD27 antibody), MGA217 (an antibody that targets B7-H3), lirilumab (a MR antibody), BMS-986016 (a LAG-3 antibody), urelumab (a 4-1BB/CD137 antibody), TRX518 (a GITR antibody), and MK-4166 (a GITR antibody).

Another example is a cancer vaccine, designed to elicit an immune response against tumor-specific or tumor-associated antigens, encouraging the immune system to attack cancer cells bearing these antigens. Exemplary agents are AGS-003, DCVax, and NY-ESO-1.

Another example is immune cells are removed from a patient, genetically modified or treated with chemicals to enhance their activity, and then re-introduced into the patient with the goal of improving the immune system's anti-cancer response.

In the context of the methods described herein, the amount of apilimod administered to the subject is a therapeutically effective amount. The term "therapeutically effective amount" refers to an amount sufficient to treat, ameliorate a symptom of, reduce the severity of, or reduce the duration of the disease or disorder being treated or enhance or improve the therapeutic effect of another therapy, or sufficient to exhibit a detectable therapeutic effect in the subject. In one embodiment, the therapeutically effective amount of an apilimod composition is the amount effective to inhibit PIKfyve kinase activity.

An effective amount of apilimod can range from about 0.001 mg/kg to about 1000 mg/kg, about 0.01 mg/kg to about 100 mg·kg, about 10 mg/kg to about 250 mg/kg, about 0.1 mg/kg to about 15 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In more specific aspects, the apilimod is administered at a dosage regimen of 30-1000 mg/day (e.g., 30, 35, 40, 45, 50, 55, 60, 65, 70, 75, 80, 85, 90, 95, 100, 125, 150, 175, 200, 225, 250, 275, or 300 mg/day) for at least 1 week (e.g., 1, 2, 3, 4, 5, 6, 7, 8, 9, 10, 11, 12, 36, 48, or more weeks). Preferably, apilimod is administered at a dosage regimen of 100-1000 mg/day for 4 or 16 weeks. Alternatively or subsequently, apilimod is administered at a dosage regimen of 100-300 mg twice a day for 8 weeks, or optionally, for 52 weeks. Alternatively or subsequently, an apilimod composition is administered at a dosage regimen of 50 mg-1000 mg twice a day for 8 weeks, or optionally, for 52 weeks.

An effective amount of the apilimod composition can be administered once daily, from two to five times daily, up to two times or up to three times daily, or up to eight times daily. In one embodiment, the apilimod composition is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In accordance with the methods described herein, a "subject in need thereof" is a subject having renal cancer, or a subject having an increased risk of developing renal cancer relative to the population at large. The subject in need thereof can be one that is "non-responsive" or "refractory" to a currently available therapy for the cancer. In this context, the terms "non-responsive" and "refractory" refer to the subject's response to therapy as not clinically adequate to relieve one or more symptoms associated with the disease or disorder. In one aspect of the methods described here, the subject in need thereof is a subject having cancer whose cancer is refractory to standard therapy or whose cancer has recurred following standard treatment.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The term "patient" refers to a human subject.

The present disclosure also provides a monotherapy for the treatment of renal cancer as described herein. As used herein, "monotherapy" refers to the administration of a single active or therapeutic compound to a subject in need thereof.

As used herein, "treatment", "treating" or "treat" describes the management and care of a patient for the purpose of combating a disease, condition, or disorder and includes the administration of apilimod to alleviate the symptoms or complications of a disease, condition or disorder, or to eliminate the disease, condition or disorder.

As used herein, "prevention", "preventing" or "prevent" describes reducing or eliminating the onset of the symptoms or complications of the disease, condition or disorder and includes the administration of apilimod to reduce the onset, development or recurrence of symptoms of the disease, condition or disorder.

In one embodiment, the administration of apilimod leads to the elimination of a symptom or complication of the cancer being treated, however elimination of the cancer is not required. In one embodiment, the severity of the symptom is decreased. In the context of cancer, such symptoms may include clinical markers of severity or progression including the degree to which a tumor secretes growth factors, degrades the extracellular matrix, becomes vascularized, loses adhesion to juxtaposed tissues, or metastasizes, as well as the number of metastases.

Treating cancer according to the methods described herein can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer according to the methods described herein can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer according to the methods described herein can result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer according to the methods described herein can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer according to the methods described herein can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer according to the methods described herein can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer according to the methods described herein can result in increase in average survival time of a population of treated subjects in comparison to a population receiving monotherapy with a drug that is not apilimod. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer according to the methods described herein can result in a decrease in the mortality rate of a population of treated subjects in comparison to a population receiving carrier alone. Treating a disorder, disease or condition according to the methods described herein can result in a decrease in the mortality rate of a population of treated subjects in comparison to an untreated population. Treating a disorder, disease or condition according to the methods described herein can result in a decrease in the mortality rate of a population of treated subjects in comparison to a population receiving monotherapy with a drug that is not apilimod. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer according to the methods described herein can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time. In one embodiment, after treatment the tumor growth rate may be about zero and is determined to maintain the same size, e.g., the tumor has stopped growing.

Treating cancer according to the methods described herein can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder according to the methods described herein can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder according to the methods described herein can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder according to the methods described herein can result in a decrease in the size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. The size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder according to the methods described herein can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, apilimod acts selectively on a hyper-proliferating cells or abnormally proliferating cells, compared to normal cells. As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms. Preferably, apilimod, acts selectively to modulate one molecular target (e.g., a target kinase) but does not significantly modulate another molecular target (e.g., a non-target kinase). The disclosure also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in diseased or hyper-proliferating cells if it occurred greater than twice as frequently in diseased or hyper-proliferating cells as compared to normal cells.

Pharmaceutical Compositions and Formulations

The present disclosure provides pharmaceutical compositions comprising an amount of apilimod, or a pharmaceutically acceptable salt, solvate, clathrate, hydrate, polymorph, metabolite, prodrug, analog or derivative thereof, in combination with at least one pharmaceutically acceptable excipient or carrier, wherein the amount is effective for the treatment of renal cancer and/or effective to inhibit PIKfyve in the cancer cells of a subject having cancer.

In one embodiment, the apilimod is apilimod free base. In one embodiment, the apilimod is apilimod dimesylate.

In one embodiment, the apilimod is combined with at least one additional active agent in a single dosage form. In one embodiment, the composition further comprises an antioxidant.

In embodiments, the at least one additional active agent is selected from the group consisting of an alkylating agent, an intercalating agent, a tublin binding agent, a corticosteroid, and combinations thereof. In one embodiment, the at least one additional active agent is a therapeutic agent selected from the group consisting of ibrutinib, rituximab, doxorubicin, prednisolone, vincristine, velcade, and everolimus, and combinations thereof. In one embodiment, the at least one additional active agent is a therapeutic agent selected from cyclophosphamide, hydroxydaunorubicin (also referred to as doxorubicin or Adriamycin™), vincristine (also referred to as Oncovin™), prednisone, prednisolone, and combinations thereof.

In embodiments, the at least one additional active agent is a non-therapeutic agent selected to ameliorate one or more side effects of the apilimod composition. In one embodiment, the nontherapeutic agent is selected from the group consisting of ondansetron, granisetron, dolasetron and palonosetron. In one embodiment, the non-therapeutic agent is selected from the group consisting of pindolol and risperidone.

In embodiments, at least one additional agent is a PD-1/PDL-1 pathway inhibitor. In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In embodiments, the at least one additional active agent is selected from an inhibitor of the mTOR pathway, a TKI inhibitor, a PI3K inhibitor, a dual PI3K/mTOR inhibitor, a SRC inhibitor, a VEGF inhibitor, a Janus kinase (JAK) inhibitor, a Raf inhibitor, an Erk inhibitor, a farnesyltransferase inhibitor, a histone deacetylase inhibitor, an antimitotic agent, a multi-drug resistance efflux inhibitor, an antibiotic, and a cytokine. In one embodiment, the second therapeutic agent is a therapeutic cytokine. In one embodiment, the second therapeutic agent is Interleukin-2. In another embodiment, the second therapeutic agent is selected from a tyrosine kinase inhibitor (e.g., everolimus, bevacizumab).

In embodiments, the mTOR inhibitor is selected from the group consisting of rapamycin (also referred to as sirolimus), everolimus, temsirolimus, ridaforolimus, umirolimus, zotarolimus, AZD8055, INK128, WYE-132, Torin-1, pyrazolopyrimidine analogs PP242, PP30, PP487, PP121, KU0063794, KU-BMCL-200908069-1, Wyeth-BMCL-200910075-9b, INK-128, XL388, AZD8055, P2281, and P529. See, e.g., Liu et al. Drug Disc. Today Ther. Strateg., 6(2): 47-55 (2009).

In embodiments, the mTOR inhibitor is trans-4-[4-amino-5-(7-methoxy-1H-indol-2-yl)imidazo[5,1-f][1,2,4]triazin-7-yl]cyclohexane carboxylic acid (also known as OSI-027), and any salts, solvates, hydrates, and other physical forms, crystalline or amorphous, thereof. See US 2007/0112005. OSI-027 can be prepared according to US 2007/0112005, incorporated herein by reference. In one embodiment, the mTOR inhibitor is OXA-01. See e.g., WO 2013152342 A1.

In embodiments, the PI3K inhibitor is selected from the group consisting of GS-1101 (Idelalisib), GDC0941 (Pictilisib), LY294002, BKM120 (Buparlisib), PI-103, TGX-221, IC-87114, XL 147, ZSTK474, BYL719, AS-605240, PIK-75, 3-methyladenine, A66, PIK-93, PIK-90, AZD6482, IPI-145 (Duvelisib), TG100-115, AS-252424, PIK294, AS-604850, GSK2636771, BAY 80-6946 (Copanlisib), CH5132799, CAY10505, PIK-293, TG100713, CZC24832 and HS-173.

In embodiments, the dual PI3K/mTOR inhibitor is selected from the group consisting of, GDC-094, WAY-001, WYE-354, WAY-600, WYE-687, Wyeth-BMCL-200910075-16b, Wyeth-BMCL-200910096-27, KU0063794 and KUBMCL-200908069-5, NVP-BEZ235, XL-765, PF-04691502, GDC-0980 (Apitolisib), GSK1059615, PF-05212384, BGT226, PM-402, VS-558 and GSK2126458. See, e.g., Liu et al. Drug Disc. Today Ther. Strateg., 6(2): 47-55 (2009), incorporated herein by reference.

In embodiments, the mTOR pathway inhibitor is a polypeptide (e.g., an antibody or fragment thereof) or a nucleic acid (e.g., a double-stranded small interfering RNA, a short hairpin RNA, a micro-RNA, an antisense oligonucleotide, a locked nucleic acid, or an aptamer) that binds to and inhibits the expression level or activity or a protein (or nucleic acid encoding the protein) in the mTOR pathway. For example, the polypeptide or nucleic acid inhibits mTOR Complex 1 (mTORC1), regulatory-associated protein of mTOR (Raptor), mammalian lethal with SEC13 protein 8 (MLST8), proline-rich Akt substrate of 40 kDa (PRAS40), DEP domain-containing mTOR-interacting protein (DEPTOR), mTOR Complex 2 (mTORC2), rapamycin-insensitive companion of mTOR (RICTOR), G protein beta subunit-like (GβL), mammalian stress-activated protein kinase interacting protein 1 (mSIN1), paxillin, RhoA, Ras-related C3 botulinum toxin substrate 1 (Rad), Cell division control protein 42 homolog (Cdc42), protein kinase C α (PKCα), the serine/threonine protein kinase Akt, phosphoinositide 3-kinase (PI3K), p70S6K, Ras, and/or eukaryotic translation initiation factor 4E (eIF4E)-binding proteins (4EBPs), or the nucleic acid encoding one of these proteins.

In embodiments, the SRC inhibitor is selected from the group consisting of bosutinib, saracatinib, dasatinib, ponatinib, KX2-391, XL-228, TG100435/TG100855, and DCC2036. See, e.g., Puls et al. Oncologist. 2011 May; 16(5): 566-578. In one embodiment, the SRC inhibitor is a polypeptide (e.g., an antibody or fragment thereof) or nucleic acid (e.g., a double-stranded small interfering RNA, a short hairpin RNA, a micro-RNA, an antisense oligonucleotide, a locked nucleic acid, or an aptamer) that binds to and inhibits the expression level or activity of the SRC protein or a nucleic acid encoding the SRC protein.

In embodiments, the VEGF inhibitor is selected from bevacizumab, sunitinib, pazopanib, axitinib, sorafenib, regorafenib, lenvatinib, and motesanib. In one embodiment, the VEGF inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a VEGF protein, a VEGF receptor protein, or a nucleic acid encoding one of these proteins. For example, the VEGF inhibitor is a soluble VEGF receptor (e.g., a soluble VEGF-C/D receptor (sVEGFR-3)).

In embodiments, the JAK inhibitor is selected from facitinib, ruxolitinib, baricitinib, CYT387 (CAS number 1056634-68-4), lestaurtinib, pacritinib, and TG101348 (CAS number 936091-26-8). In one embodiment, the JAK inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a JAK (e.g., JAK1, JAK2, JAK3, or TYK2) or a nucleic acid encoding the JAK protein.

In embodiments, the Raf inhibitor is selected from PLX4032 (vemurafenib), sorafenib, PLX-4720, GSK2118436 (dabrafenib), GDC-0879, RAF265, AZ 628, NVP-BHG712, SB90885, ZM 336372, GW5074, TAK-632, CEP-32496 and LGX818 (Encorafenib). In one embodiment, the Raf inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a Raf (e.g., A-Raf, B-Raf, C-Raf) or a nucleic acid encoding the Raf protein. In one embodiment, the MEK inhibitor is selected from AZD6244 (Selumetinib), PD0325901, GSK1120212 (Trametinib), U0126-EtOH, PD184352, RDEA119 (Rafametinib), PD98059, BIX 02189, MEK162 (Binimetinib), AS-703026 (Pimasertib), SL-327, BIX02188, AZD8330, TAK-733 and PD318088. In one embodiment, the MEK inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a MEK (e.g., MEK-1, MEK-2) or a nucleic acid encoding the MEK protein.

In embodiments, the Akt inhibitor is selected from MK-2206, KRX-0401 (perifosine), GSK690693, GDC-0068 (Ipatasertib), AZD5363, CCT128930, A-674563, PHT-427. In one embodiment, the Akt inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a Akt (e.g., Akt-1, Akt-2, Akt-3) or a nucleic acid encoding the Akt protein.

In embodiments, the farnesyltransferase inhibitor is selected from LB42708 or tipifarnib. In one embodiment, the farnesyltransferase inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of farnesyltransferase or a nucleic acid encoding the farnesyltransferase protein. In one embodiment, the histone modulating inhibitor is selected from anacardic acid, C646, MG149 (histone acetyltransferase), GSK J4 Hcl (histone demethylase), GSK343 (active against EZH2), BIX 01294 (histone methyltransferase), MK0683 (Vorinostat), MS275 (Entinostat), LBH589 (Panobinostat), Trichostatin A, MGCD0103 (Mocetinostat), Tasquinimod, TMP269, Nexturastat A, RG2833, PDX101 (Belinostat).

In embodiments, the anti-mitotic agent is selected from Griseofulvin, vinorelbine tartrate, paclitaxel, docetaxel, vincristine, vinblastine, Epothilone A, Epothilone B, ABT-751, CYT997 (Lexibulin), vinflunine tartrate, Fosbretabulin, GSK461364, ON-01910 (Rigosertib), Ro3280, BI2536, NMS-P937, BI 6727 (Volasertib), HMN-214 and MLN0905.

In embodiments, the tyrosine kinase inhibitor is selected from Votrient, Axitinib, Bortezomib, Bosutinib, Carfilzomib, Crizotinib, Dabrafenib, Dasatinib, Erlotinib, Gefitinib, Ibrutinib, Imatinib, Lapatinib, Nilotinib, Pegaptanib, Ponatinib, Regorafenib, Ruxolitinib, Sorafenib, Sunitinib, Trametinib, Vandetanib, Vemurafenib, and Vismodegib.

In one embodiment, the polyether antibiotic is selected from sodium monensin, nigericin, valinomycin, salinomycin.

A "pharmaceutical composition" is a formulation containing the compounds described herein in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

Example 1: Apilimod is a Highly Selective Inhibitor of TSC2 Null Cell Proliferation Apilimod was identified in a high throughput cell viability screen using TSC2−/− mouse embryonic fibroblasts (MEF-EV) cells. TSC2 null cells have constitutively active mTOR. Briefly, MEF cells derived from TSC2−/− knockout mouse embryos (Onda et al., *J. Clin. Invest.* 104(6):687-95, 1999) were infected with a retrovirus vector encoding the hygromycin antibiotic resistance gene (MEF-EV) or the same retrovirus vector also encoding TSC2 (MEF-TSC2). The MEF-EV and MEF-TSC2 line were then established by hygromycin selection.

Cells were expanded in DMEM containing 10% FBS (Omega Scientific) and 2 mM L-Glutamine. Frozen stocks of cells were prepared for direct use in the HTS assay. Cells were harvested, pelleted and then resuspended in 95% FBS & 5% DMSO at a concentration $1 \times 10^7$ cells/ml., One ml aliquots were rate frozen to −80 at a rate of 1 degree per minute. These stocks were then transferred to vapor phase liquid nitrogen for long term storage.

For screening, vials were thawed at 37° C. with continuous agitation until just thawed then re-suspended in room temperature assay media and centrifuged at 1,000 rpm for 5 minutes. The resulting pellet was re-suspended in appropriate volume and counted using an automated cell counter and diluted accordingly to a final count of 40,000 cells/ml.

Test compounds (5 µl stock solution, 6× desired final well concentration) were dispensed to 384-well assay plates (Corning 3712) using a Biomek FX liquid handler. MEF-EV cells (1000 cells per well in 25 µL of media) were added to these pre-formatted plates using a Thermo Wellmate, non-contact dispensing system with a standard bore cassette head. Plates were incubated for 72h at 37° C. under an atmosphere of 5% $CO_2$ in a humidified incubator.

Cell viability was determined with CellTiter-Glo® luminescence assay (Promega) as per the manufacturer's instructions. Viability was expressed as a percentage of untreated control cells. As an example, for apilimod, MEF-EV cell viability (Mean+/−StDev, n=3) was 2.16+/−0.36% @ 0.5 µM and 1.94+/−0.07% @ 5 µM.

The activity of apilimod on TSC2 deficient cells was further demonstrated by performing 10 point dose response on the MEF-EV and MEF-TSC2 lines described above as well as three additional pairs of isogenic lines: (1) (TSC2−/−, p53−/−) and (TSC2+/−, p53−/−) MEF lines were established from (TSC2−/−, p53−/−) or (TSC2+/−, p53−/−) embryos according to standard methods. See e.g., Zhang et al. *J. Clin. Invest.* 112, 1223-33, 2003. (2) ELT3-EV and ELT3-TSC2 lines were established from the ELT3 rat tumor cell line. The ELT3 line is an established rat tumor model for LAM/TSC. See e.g., Howe et al., *Am. J. Path.* 146, 1568-79, 1995. These cells harbor an inactivating mutation in TSC2, which leads to constitutive activation of the mTOR pathway. To develop an isogenic pair of cells ELT3 cells were infected with a retrovirus vector encoding the hygromycin antibiotic resistance gene (ELT3-EV) or the same retrovirus vector also encoding TSC2 (ELT3-TSC2). The ELT3-EV and ELT3-TSC2 line were then established by hygromycin selection. (3) TRI-AML102 and AML103 lines were established from a TSC2 null primary human AML sample provided by Dr. Elizabeth Henske (Fox Chase Cancer Center, Philadelphia, Pa.). The cells were infected with amphotropic retrovirus LXSN16E6E7 that encodes the HPV16 E6 and E7 open reading frames and neomycin resistance cassette. Cells were expanded and neomycin-selected. Individual clones were isolated and frozen down. The coding sequence for the human Telomerase gene (hTERT) with hygromycin resistance cassette (pLXSN hTERT-hyg plasmid) was stably expressed into a $TSC2^{-/-}$ confirmed E6E7 AML clone using Fugene6 transfection reagent (Roche Applied Science, Indianapolis, Ind.). TRI-AML102 was generated by stable incorporation of a control zeomycin selection plasmid (pcDNA3.1-zeo), while TRI-AML103 expresses the human TSC2 cDNA pcDNA3.1-zeo plasmid. As a result of these engineering processes, both TRI102 and TRI103 are neomycin, hygromycin, and zeomycin resistant lines.

For 10-point dose response, 750 MEF, 2000 ELT3, or 2000 AML cells in 100 µL of growth media (DMEM (CellGro 10-017-CV) FBS 10% (Sigma Aldrich F2442-500ML, Lot 12D370) Penicillin/Streptomycin (100×) (Cell-Gro Ref 30-002) were plated per well of a 96 well plate. 24 hours after plating cells, the media was removed and apilimod dilutions (1-500 nM, 2-fold dilutions) in 100 µL of growth media were added (0.1% final DMSO concentration). 72 hours after compound addition, relative cell viability was determined by CellTiter-Glo® luminescence assay (Promega) and expressed as a percentage relative to vehicle (DMSO) treated control cells. $IC_{50}$ values were then calculated from the dose response curves using XLFIT (IDBS).

The TSC2 deficient cells were highly sensitive to apilimod ($IC_{50}$=20 nM, FIG. 1). TSC2−/− p53−/− MEFs demonstrated increased sensitivity to apilimod compared to the TSC2+/−p53−/− MEFs as indicated by a selectivity ratio above 1 (2.45).

TABLE 1

IC$_{50}$ (viability) of apilimod in various cell types

| | Cell type: | | | |
|---|---|---|---|---|
| | MEF TSC2−/− | MEF TSC2−/− p53−/− | AML TSC2+/− p53−/− | ELT3 |
| IC50 TSC2−/− | 19.70 | 28.80 | 117.00 | 13.70 |
| IC50 TSC2 rescue | 20.10 | 70.70 | 132.00 | 16.05 |
| Selectivity Ratio | 1.02 | 2.45 | 1.13 | 1.17 |

IC50s (nM) calculated from 10-point dose response on TSC2 −/− deficient and rescue lines. IC50s are calculated from the average of two experiments. The selectivity ratio is calculated by dividing the IC50 of the TSC2 rescue line by the TSC2−/− line.

Figure 2B:
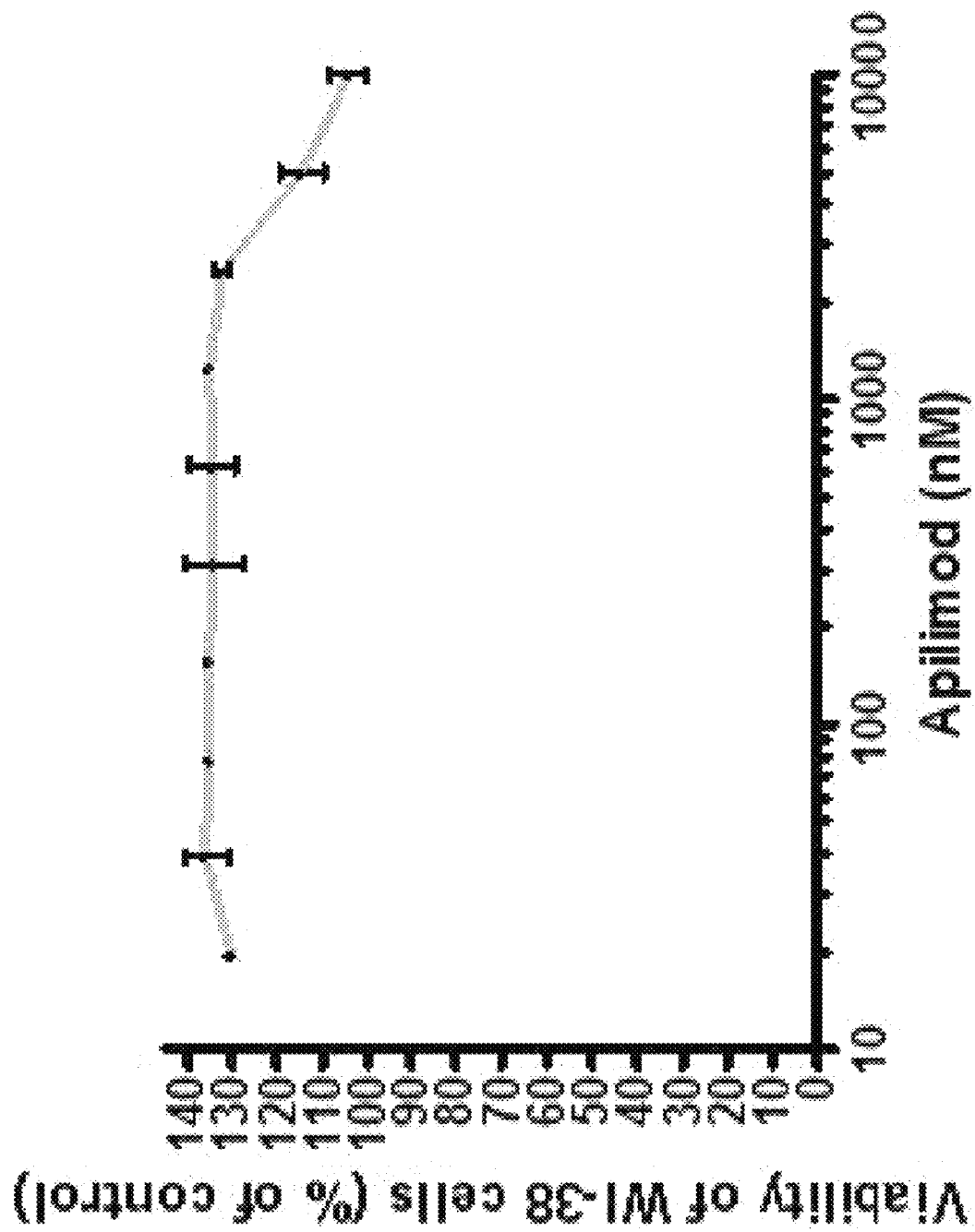

Furthermore, higher concentrations of apilimod had higher potency on the TSC2−/− MEF-EV cells compared to the TSC2 rescue MEF-TSC2 cells. This data, coupled to the fact that apilimod is not cytotoxic on peripheral blood mononuclear cells (Wada et al., *Blood* 109, 1156-64, 2007), nor on a variety of other cancer lines including U937, HELA, Jurkat, and THP-1 (PCT Publication No. WO 2006/128129) suggests that there will be a high therapeutic index for treating TSC2−/− cancer cells with apilimod (FIG. 2A-2B).

Example 2: Apilimod is a Highly Selective Cytotoxic Agent in Cancer Cells

The cytotoxic activity of apilimod was evaluated using a standard cell viability assay such as CellTiterGlo™ according to the manufacturer's instructions. 122 human cancer cell lines were evaluated for sensitivity to apilimod. A cell line was called as apilimod sensitive if the IC$_{50}$ was less than 500 nM. 35 cell lines were identified as sensitive to apilimod-induced cytotoxicity. Apilimod was also highly selective for cancer cells compared to normal cells, which had IC$_{50}$'s ranging from 20-200 fold higher than the cancer cells (FIGS. 2A-2B).

Figure 3:
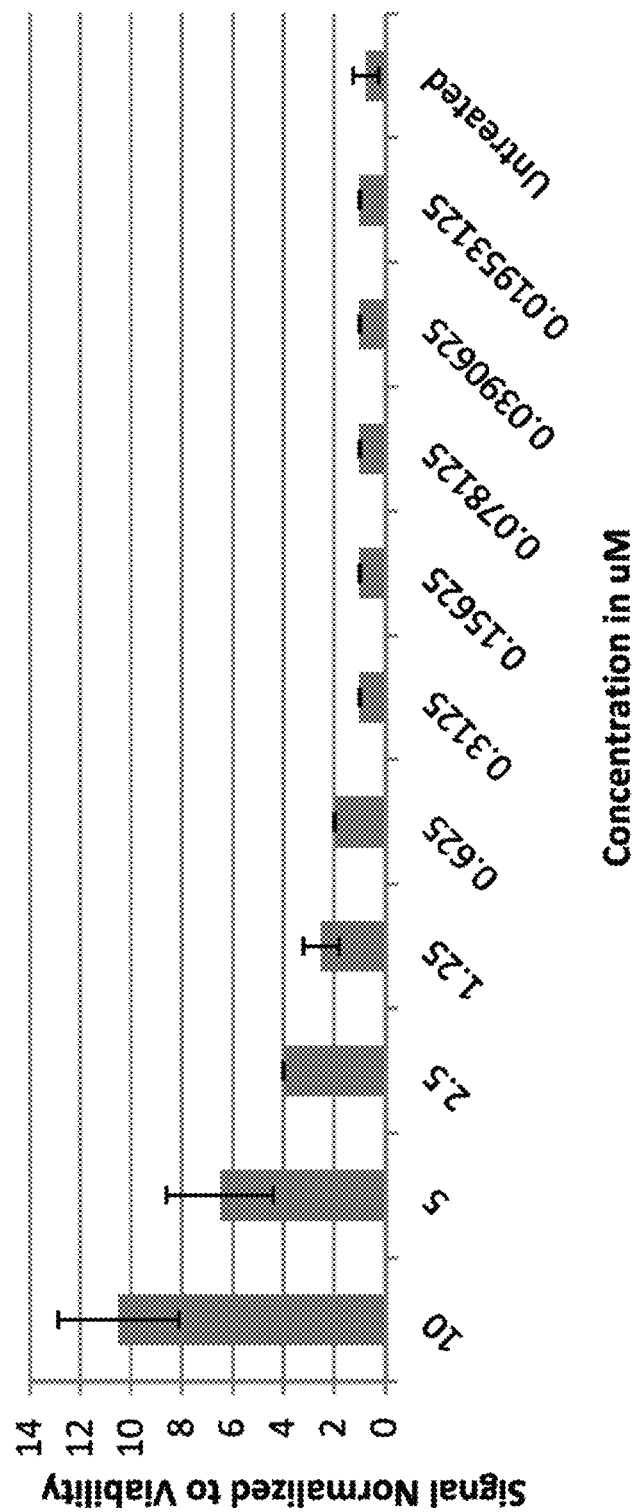
FIG. 3: apilimod induces autophagy in a dose-dependent manner.

The mechanism of apilimod's cytotoxic activity was further investigated by assaying for autophagic vacuoles after 72 hours of treatment in an H4 neuroglioma cell line (IC$_{50}$ 250-300 nM). Autophagy was quantified using the Cyto-ID Autophagy detection kit (Enzo) according to manufacturer's directions. FIG. 3 shows that apilimod induced autophagy in a dose-dependent manner.

Example 3: Apilimod is a Highly Selective Binder of PIKfyve Kinase

In order to identify the cellular target of apilimod in cancer cells, whole cell lysate prepared from human neuroglioma cells was used to identify its binding partners using chemical capture mass spectrometry (CCMS). This work was performed at Caprotec Bioanalytics GmbH, Berlin Germany. See Michaelis et al., *J. Med. Chem.*, 55 3934-44 (2012) and references cited therein.

Figure 4:
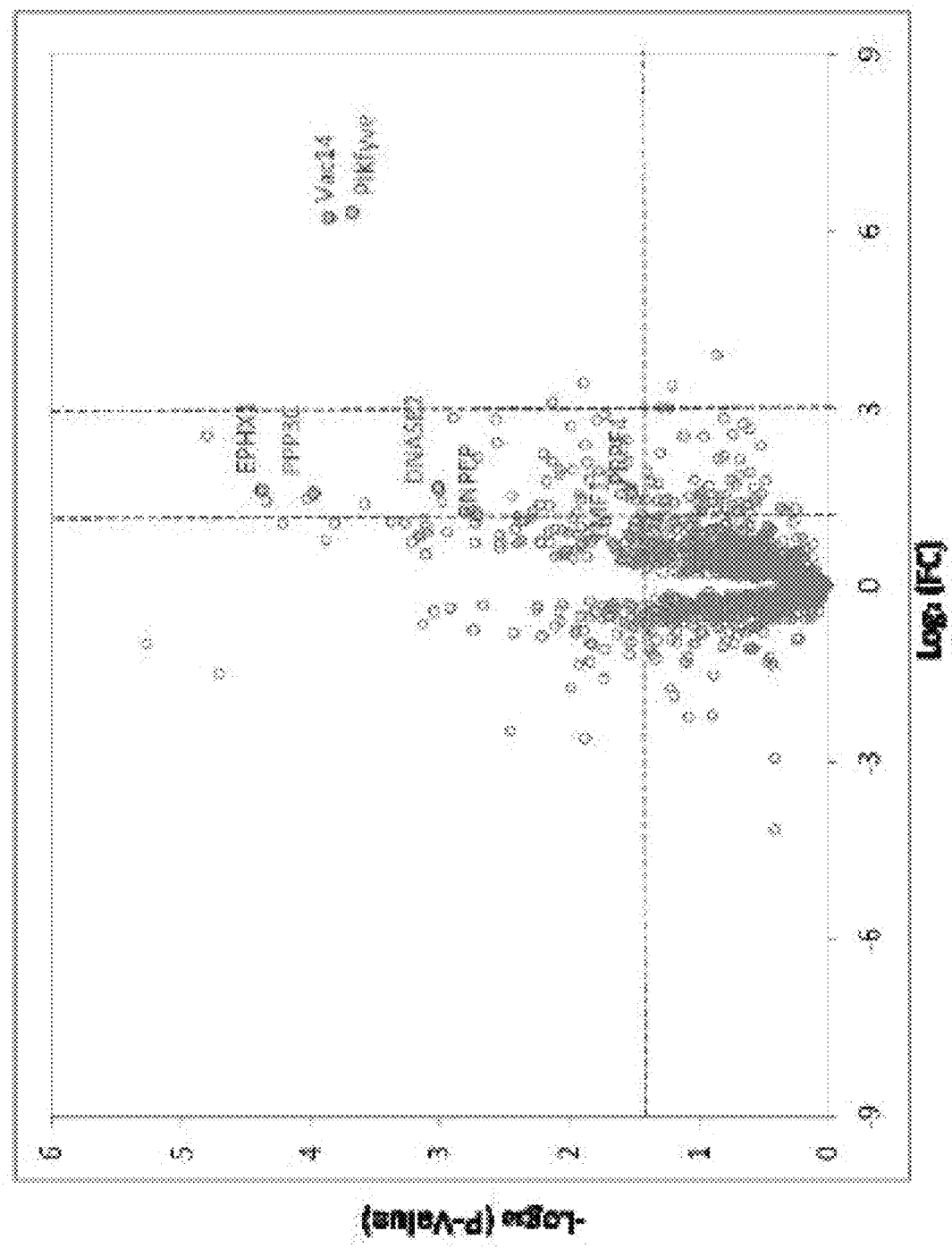
FIG. 4: Volcano plot of significant captured hits applying CT-689 at 0.1 μM concentration under optimized capture conditions.

Briefly, two capture compound variants employing apilimod as selectivity function attached in a single orientation were synthesized and analyzed by LC-MS and 1H-NMR to ensure identity and purity. Capture conditions were optimized in whole cell lysate from H4 (human neuroglioma) cancer cells, e.g. minimization of non-specific interactions of the proteins with capture compounds, concentration of reagents and proteins to obtain maximum binding of proteins and capture compounds, etc. One capture compound was selected to identify specific protein binders in the CCMS experiments using apilimod as a competitor ligand. Proteins that are detected by LC-S in the capture assay and that are significantly diminished in competition control experiments are considered to be specific binders. These specific binders were further subjected to stringent data analysis criteria to determine specificity after unbiased data evaluation. Specific protein binders were ranked according to their fold change (FC) values in the capture experiments. Only two proteins were identified as high probability candidate target proteins of apilimod: PIKfyve and Vac14. Volcano plot is shown in FIG. 4. FC and p-values for these proteins in the four different capture compound concentration experiments are shown in Table 2.

TABLE 2

| | Capture Compound Concentrations | | | | |
|---|---|---|---|---|---|
| | | 0.1 μM | 0.5 μM | 1.0 μM | 2.0 μM |
| PIKfyve | log$_2$ (FC) | 6.3 | 6.2 | 4.1 | 4.3 |
| | −log$_{10}$ (p-value) | 3.7 | 2.8 | 5.1 | 3.9 |
| Vac14 | log (FC) | 6.2 | 5.6 | Inf. | 3.9 |
| | −log$_{10}$ (p-value) | 3.9 | 3.8 | 1.9 | 3.6 |

Figure 5:
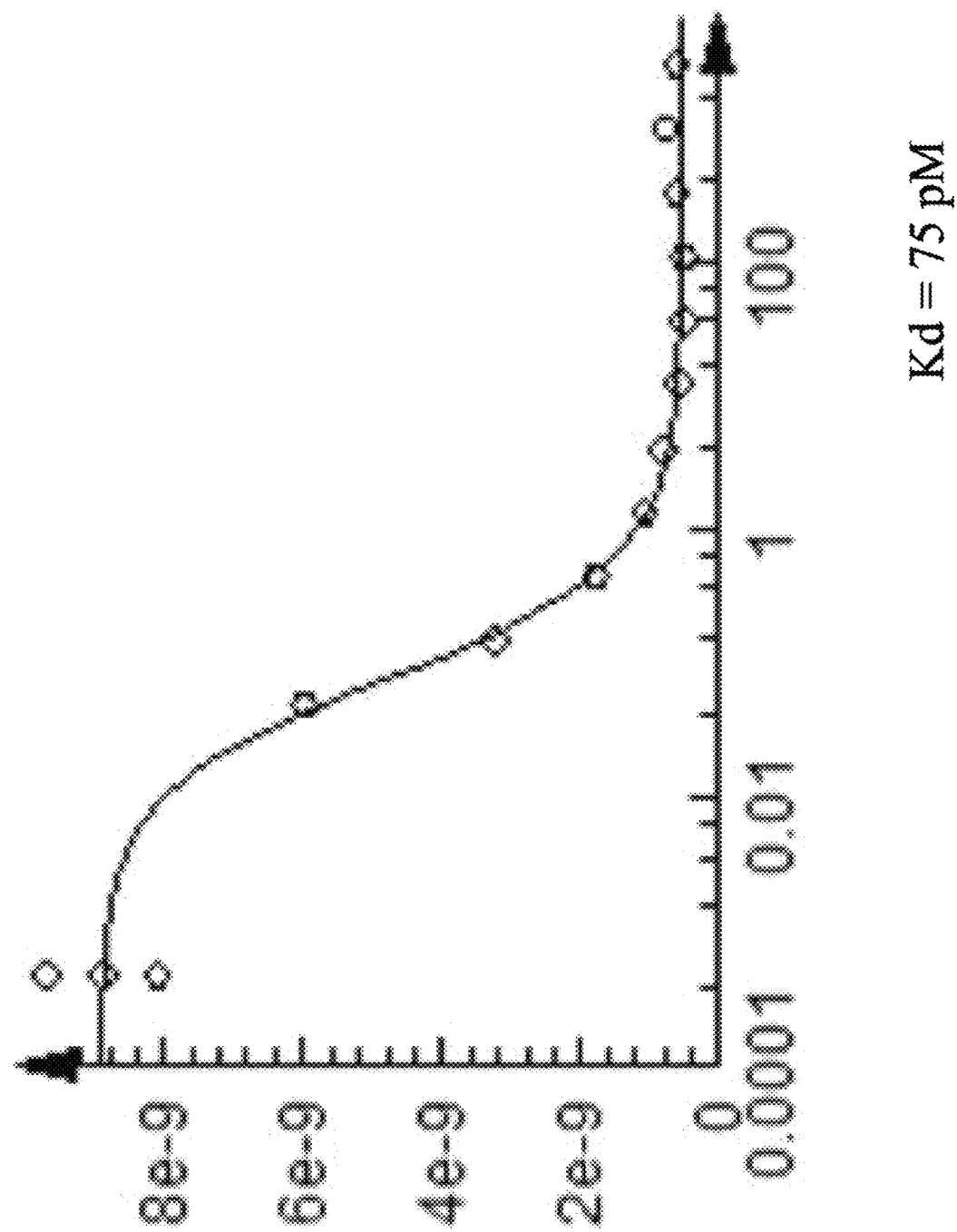
FIG. 5: apilimod binds with high affinity to PIKfyve (Kd=75 pM).
Figure 6:
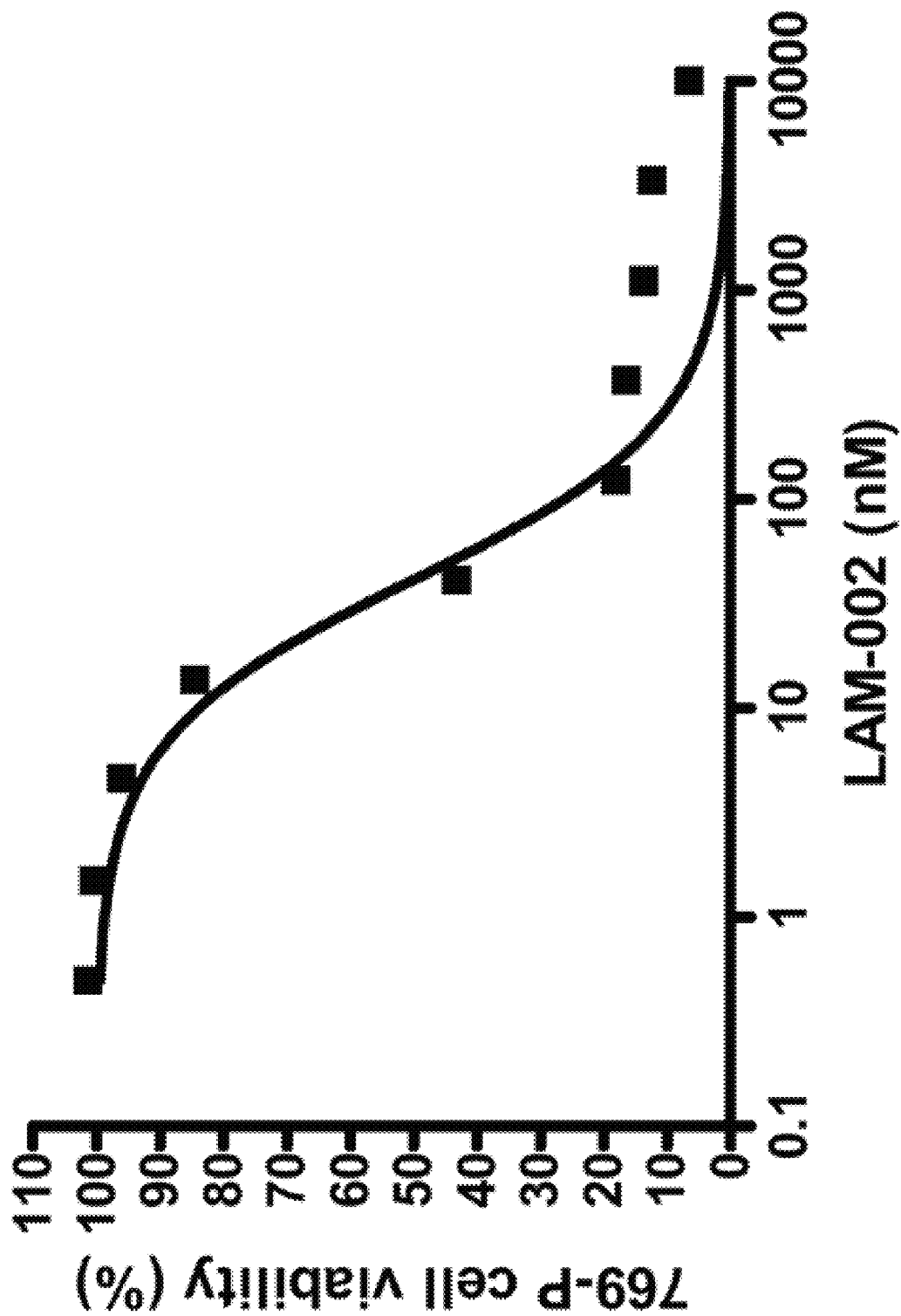
FIG. 6: antiproliferative activity of LAM-002 in renal clear cell carcinoma cell line 769-P, Avg. $IC_{50}$=44 nM (n=2).
Figure 7:
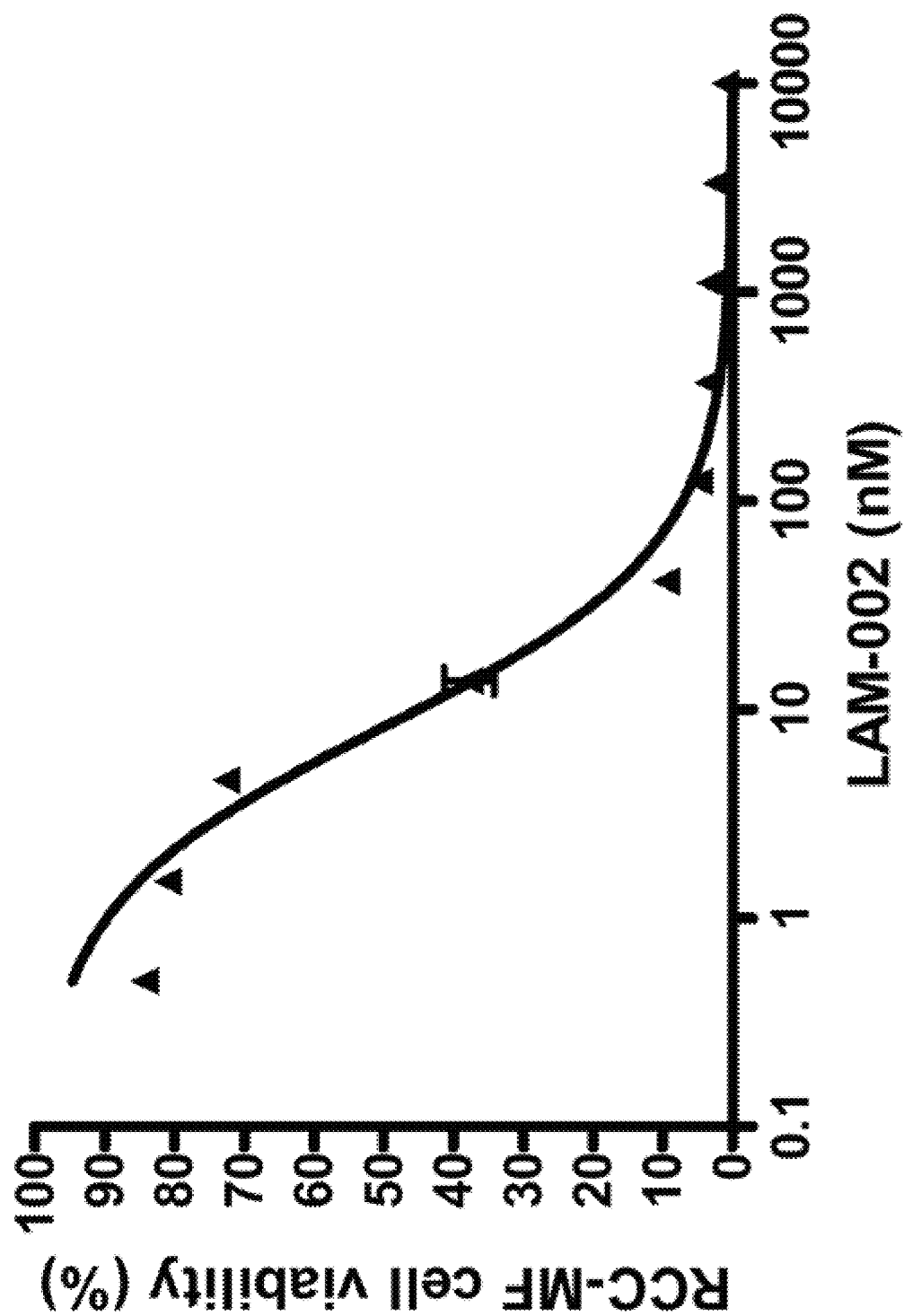
FIG. 7: antiproliferative activity of LAM-002 in renal clear cell carcinoma cell line RCC-MF, Avg. $IC_{50}$=8 nM (n=2).
Figure 8:
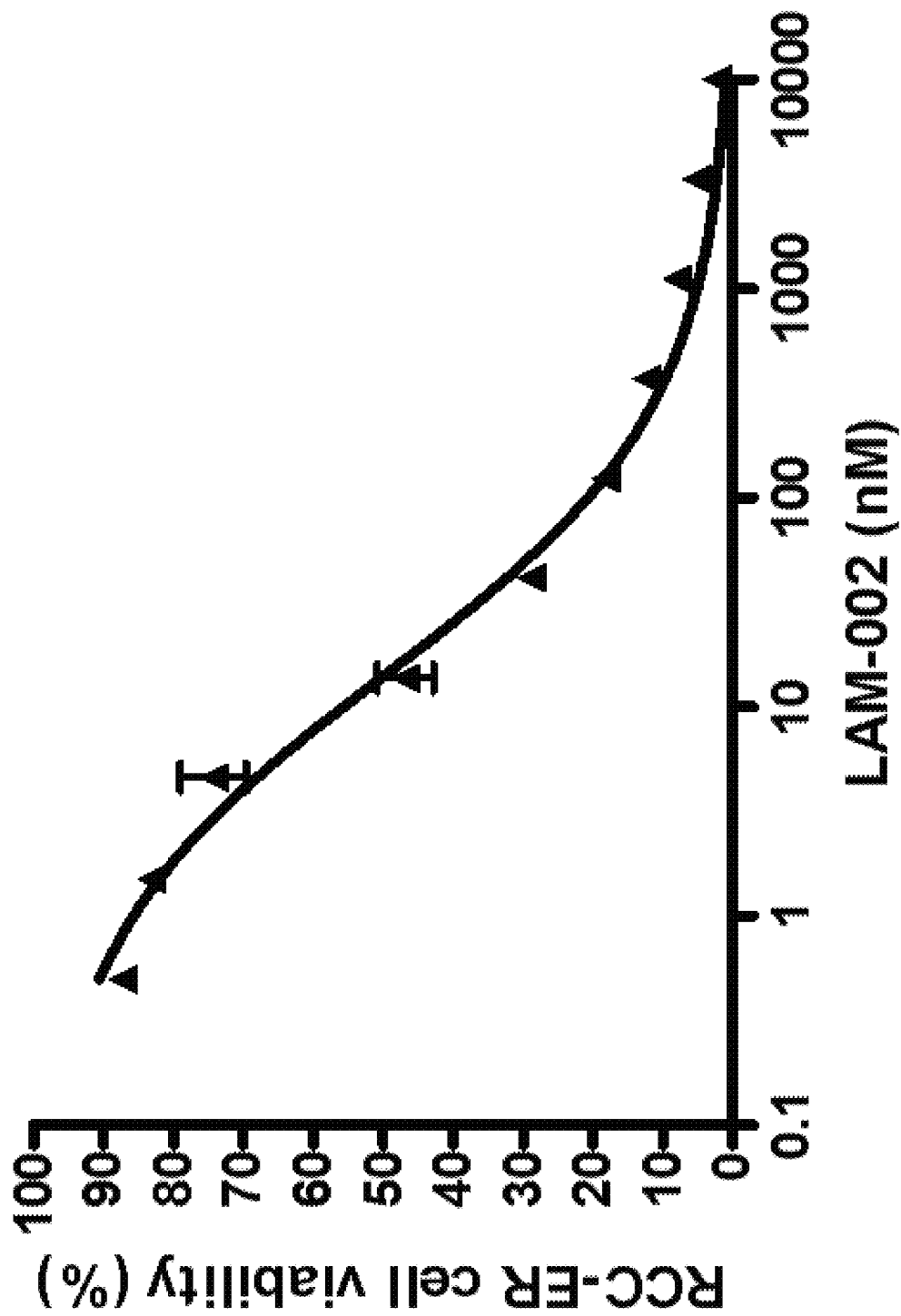
FIG. 8: antiproliferative activity of LAM-002 in renal clear cell carcinoma cell line RCC-ER, Avg. $IC_{50}$=9 nM (n=2).
Figure 9:
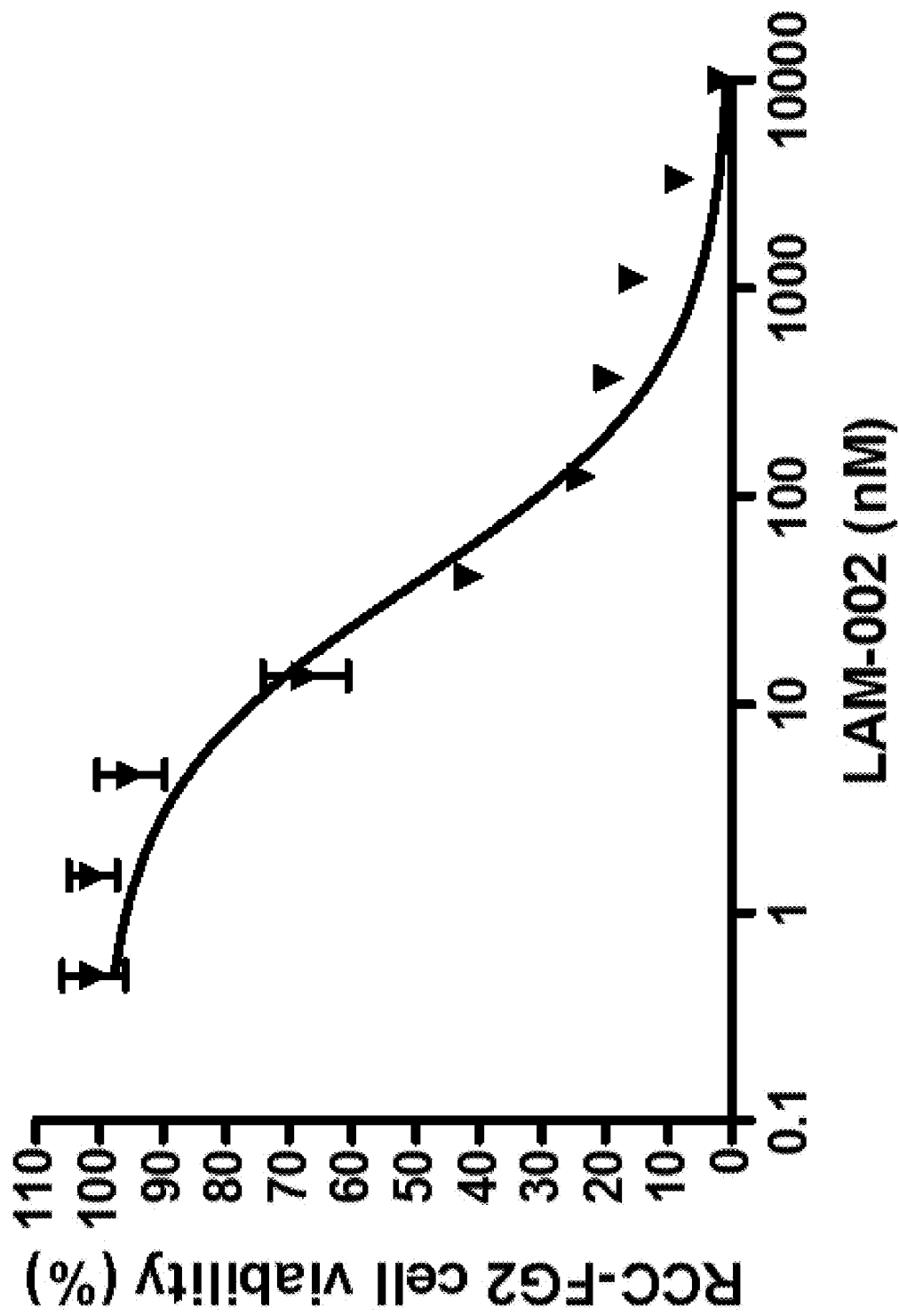
FIG. 9: antiproliferative activity of LAM-002 in renal clear cell carcinoma cell line RCC-FG2, Avg. $IC_{50}=32$ nM (n=2).
Figure 10:
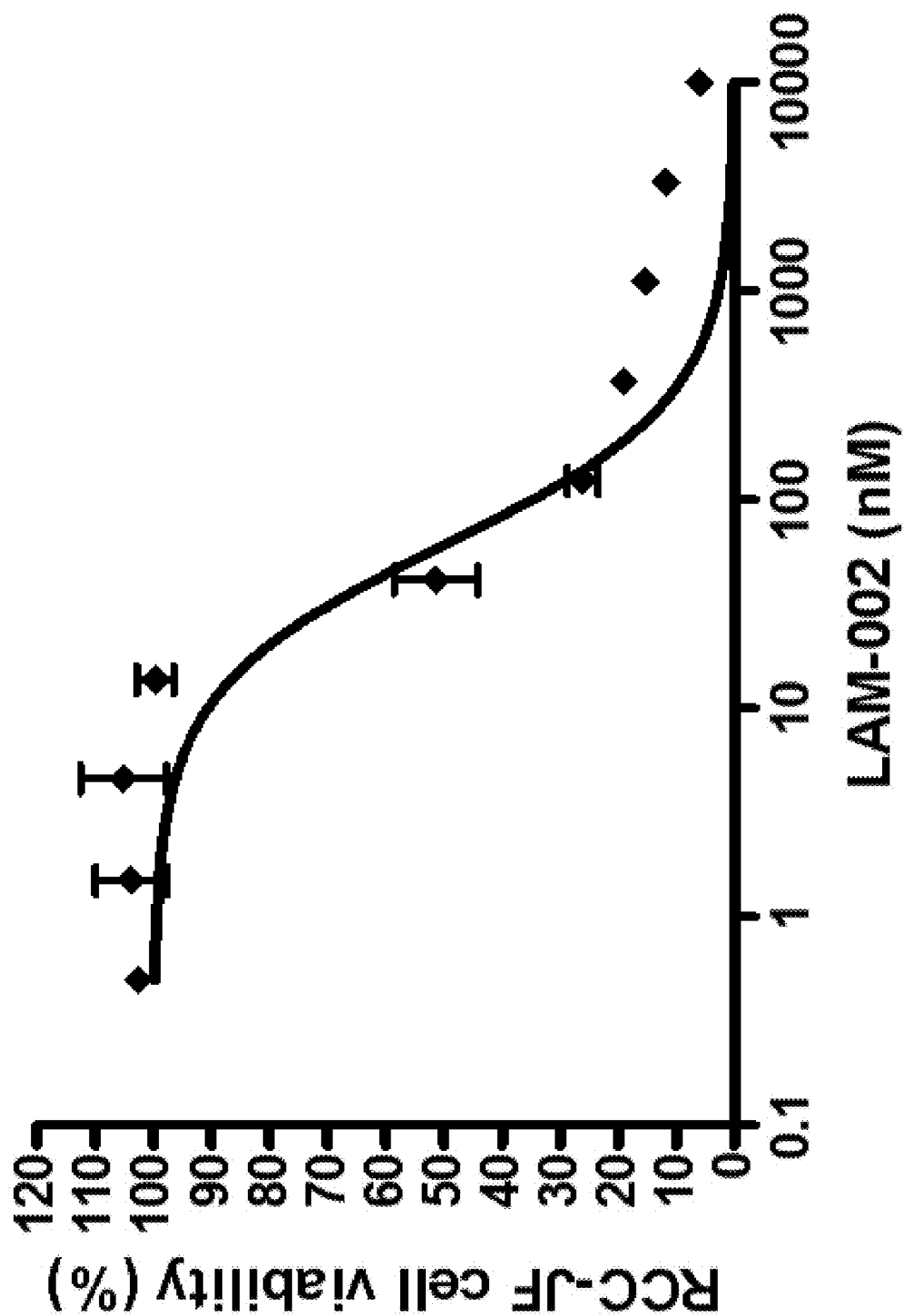
FIG. 10: antiproliferative activity of LAM-002 in renal clear cell carcinoma cell line RCC-JF, Avg. $IC_{50}=60$ nM (n=2).
Figure 11:
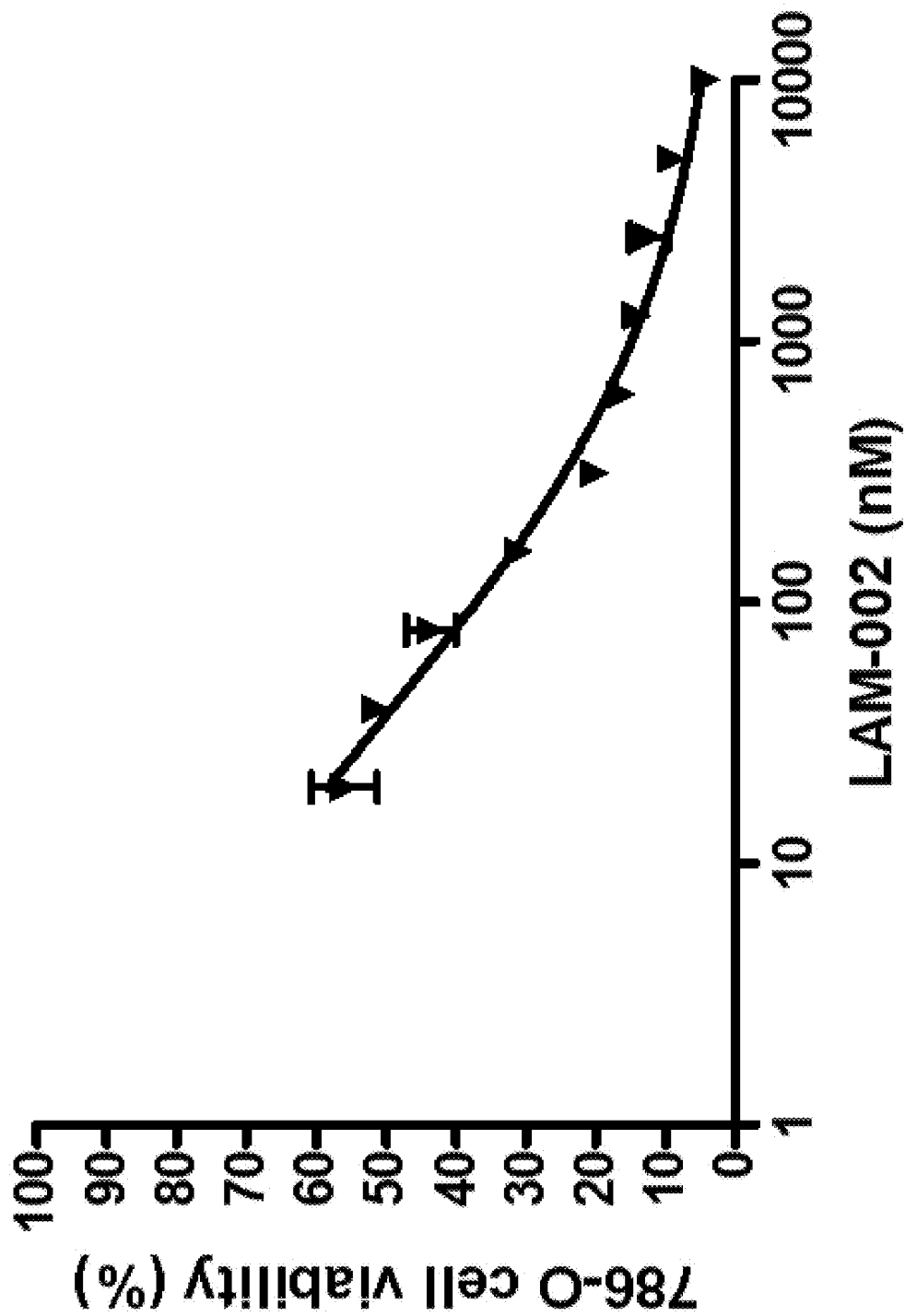
FIG. 11: antiproliferative activity of LAM-002 in renal clear cell carcinoma cell line 786-O, Avg. $IC_{50}=71$ nM (n=2).
Figure 12:
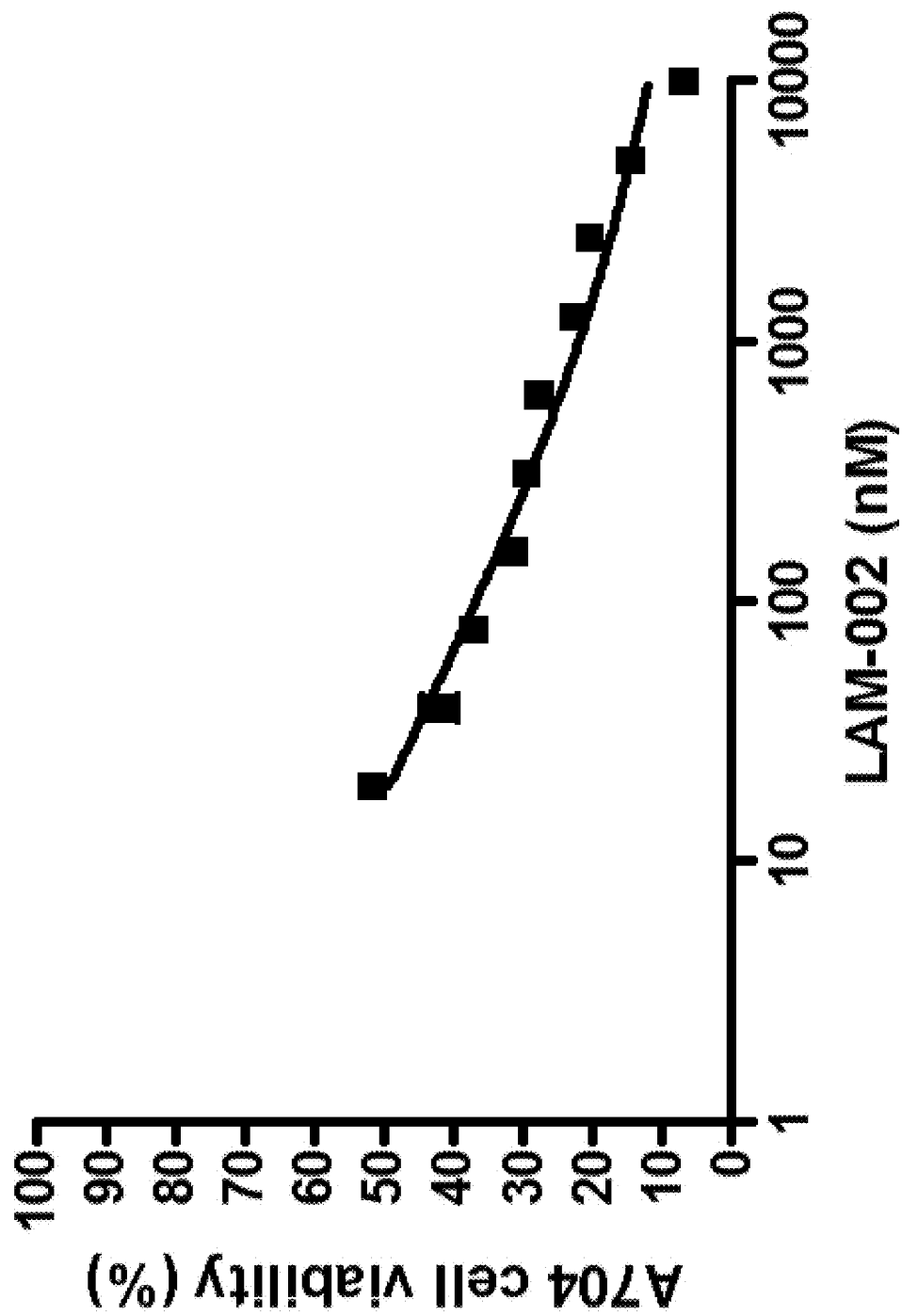
FIG. 12: antiproliferative activity of LAM-002 in renal clear cell carcinoma cell line A704, Avg. $IC_{50}=11$ nM (n=2).
Figure 13:
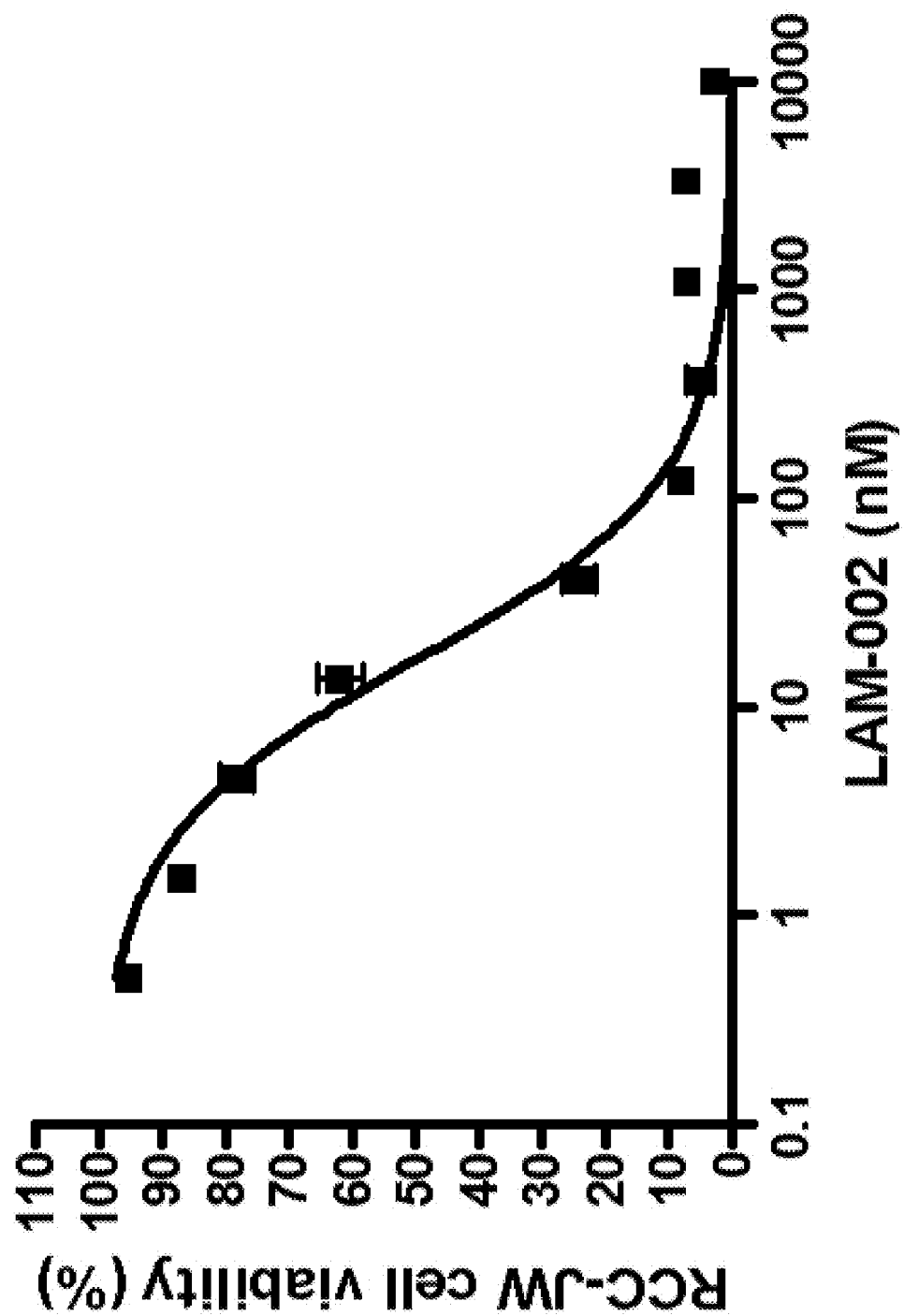
FIG. 13: antiproliferative activity of LAM-002 in renal clear cell carcinoma cell line RCC-JW, Avg. $IC_{50}=27$ nM (n=2).
Figure 14A:
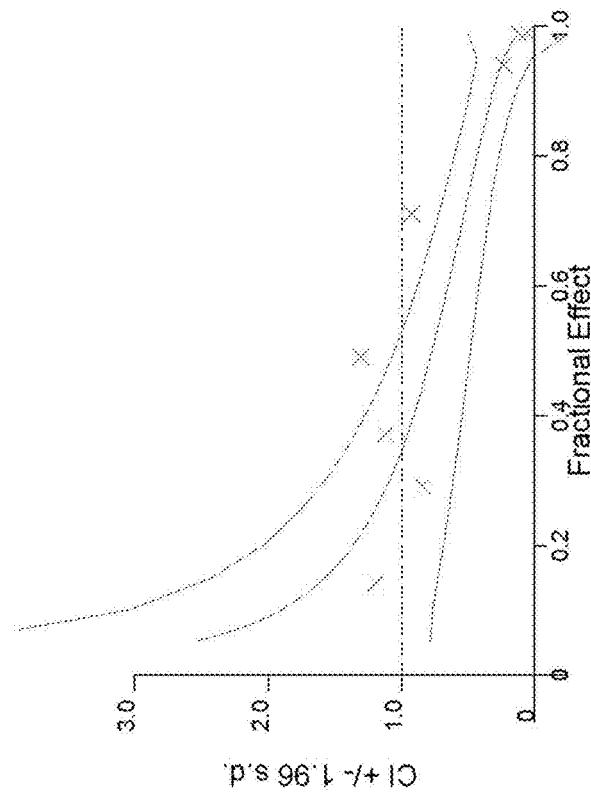
FIGS. 14A-B: LAM-002+sorafenib combination in RCC-ER cells (5 day assay). A, bar graph showing cell viability (%); B, determination of the combination index (CI) value at $ED_{50}$, $ED_{75}$ and $ED_{90}$.
Figure 14B:
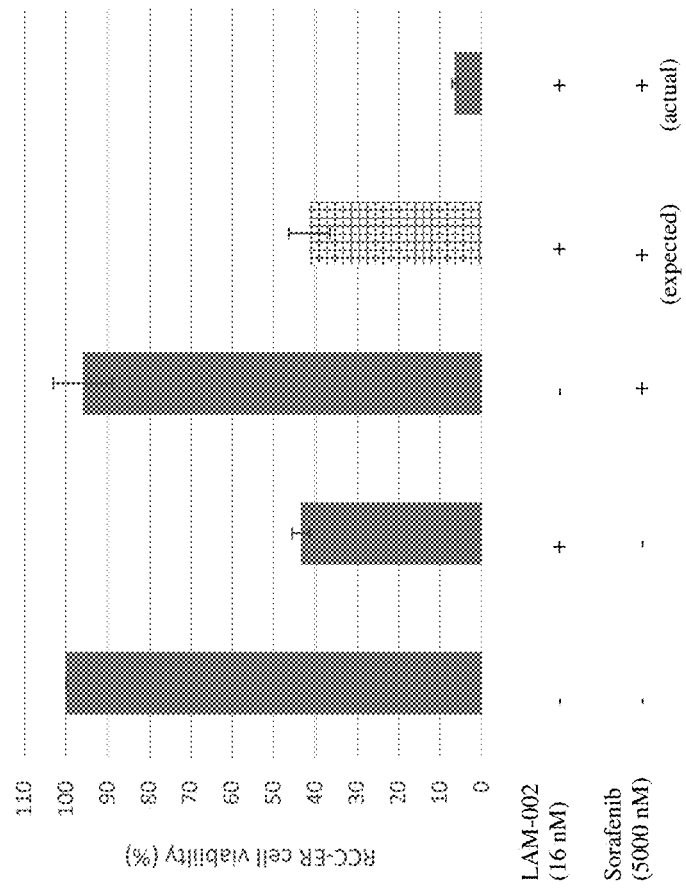
Figure 15B:
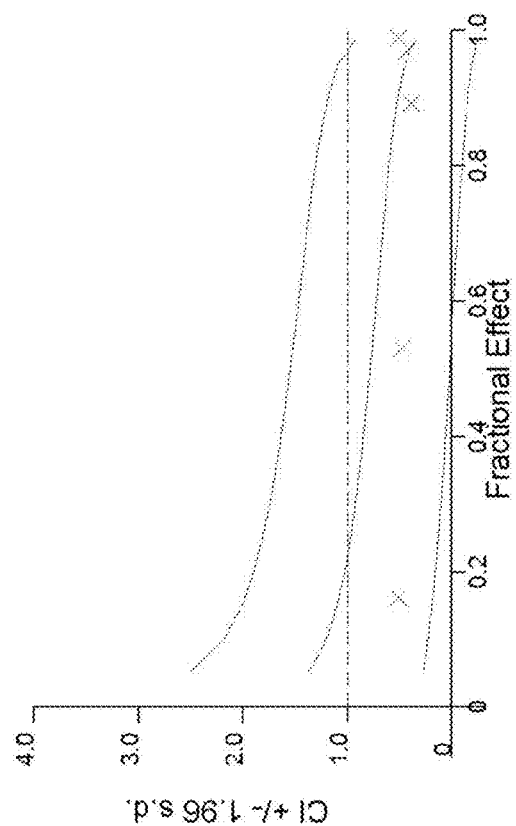
FIGS. 15A-B: LAM-002+sorafenib combination in RCC-FG2 cells (5 day assay). A, bar graph showing cell viability (%); B, determination of the combination index (CI) value at $ED_{50}$, $ED_{75}$ and $ED_{90}$.
Figure 15A:
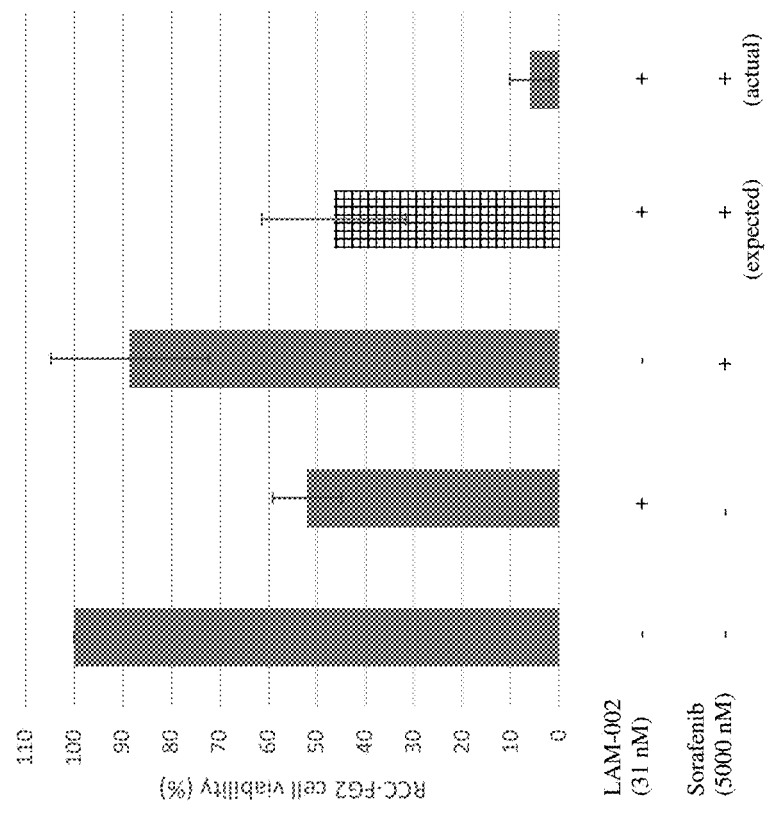
Figure 16B:
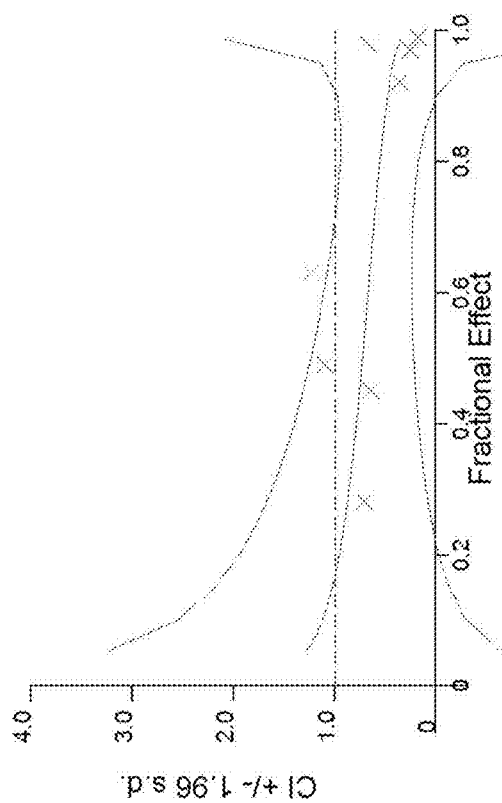
FIGS. 16A-B: LAM-002+sorafenib combination in RCC-MF cells (5 day assay). A, bar graph showing cell viability (%); B, determination of the combination index (CI) value at $ED_{50}$, $ED_{75}$ and $ED_{90}$.
Figure 16A:
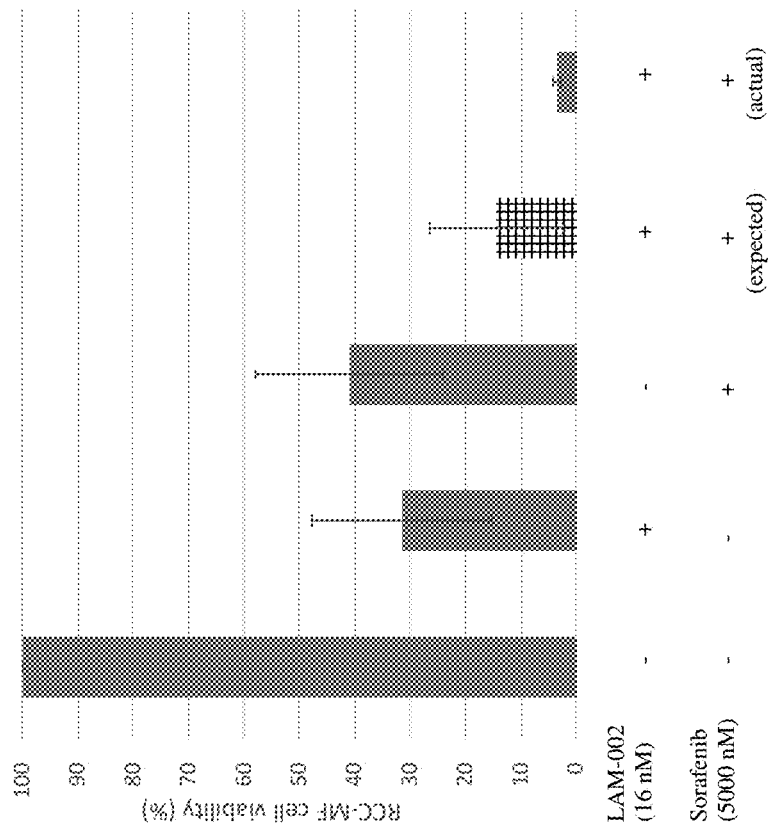
Figure 17B:
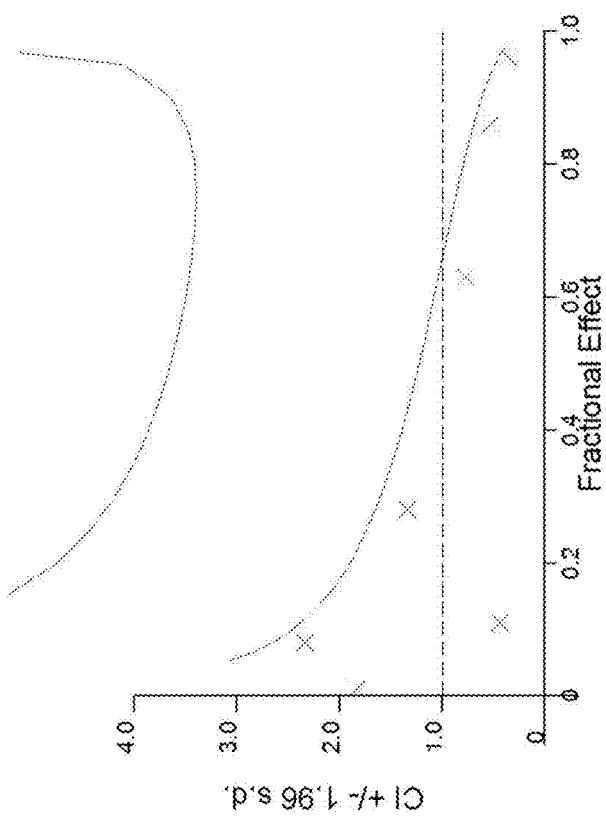
FIGS. 17A-B: LAM-002+sorafenib combination in 769-P cells (5 day assay). A, bar graph showing cell viability (%); B, determination of the combination index (CI) value at $ED_{50}$, $ED_{75}$ and $ED_{90}$.
Figure 17A:
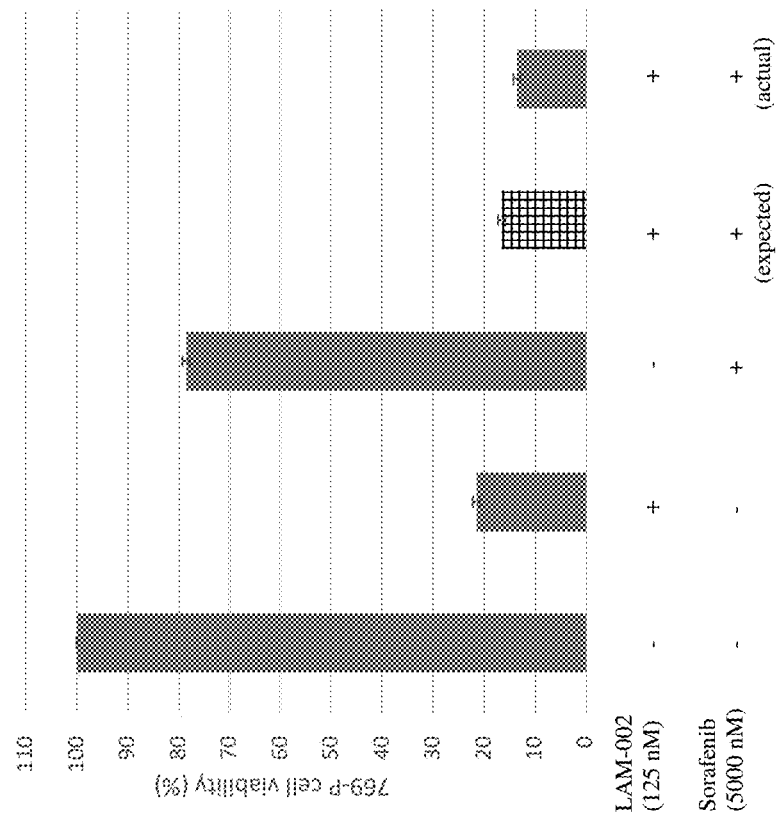
Figure 18B:
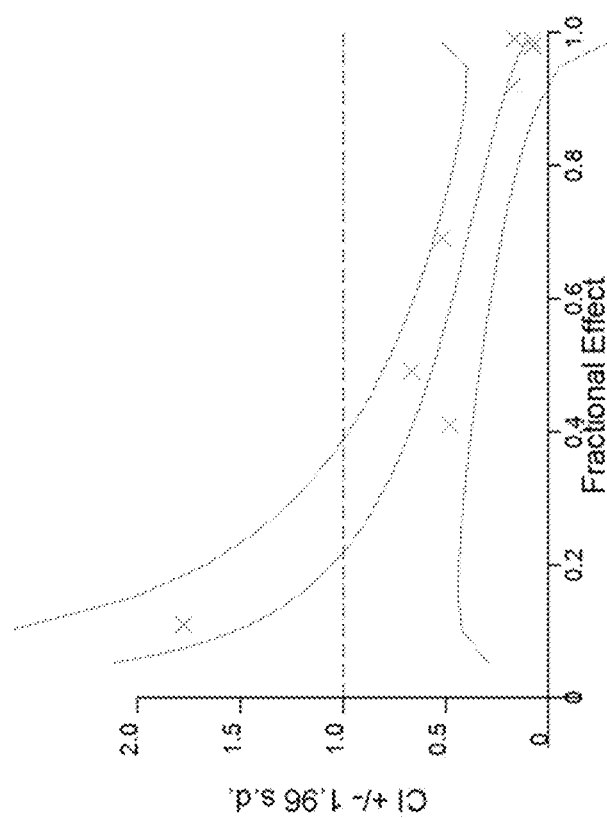
FIGS. 18A-B: LAM-002+pazopanib combination in RCC-ER cells (5 day assay). A, bar graph showing cell viability (%); B, determination of the combination index (CI) value at $ED_{50}$, $ED_{75}$ and $ED_{90}$.
Figure 18A:
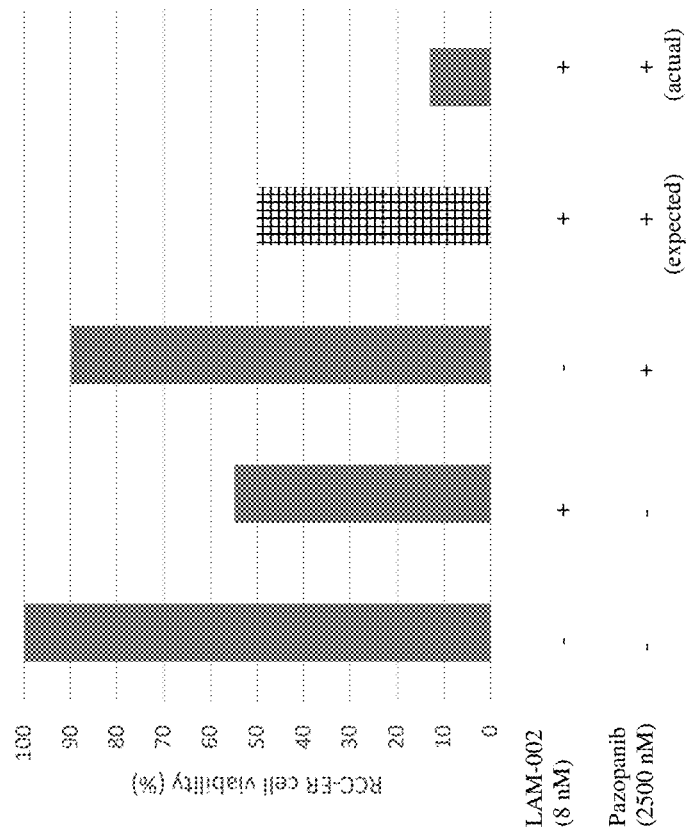
Figure 19B:
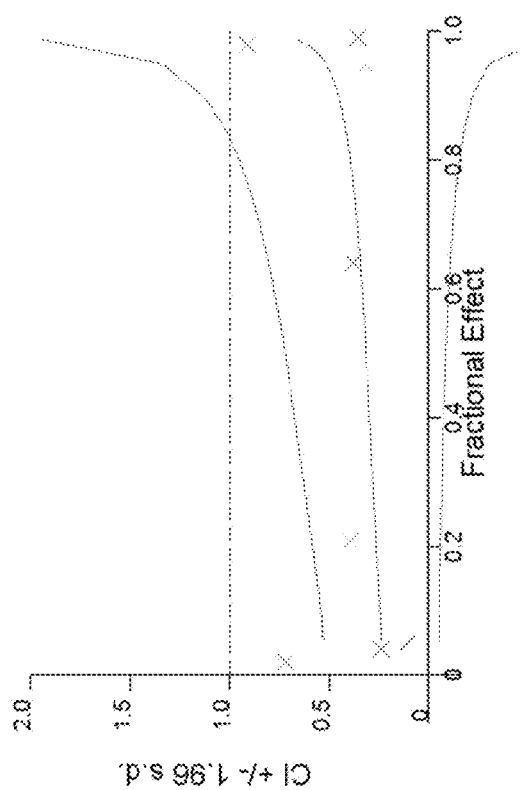
FIGS. 19A-B: LAM-002+pazopanib combination in RCC-FG2 cells (5 day assay). A, bar graph showing cell viability (%); B, determination of the combination index (CI) value at $ED_{50}$, $ED_{75}$ and $ED_{90}$.
Figure 19A:
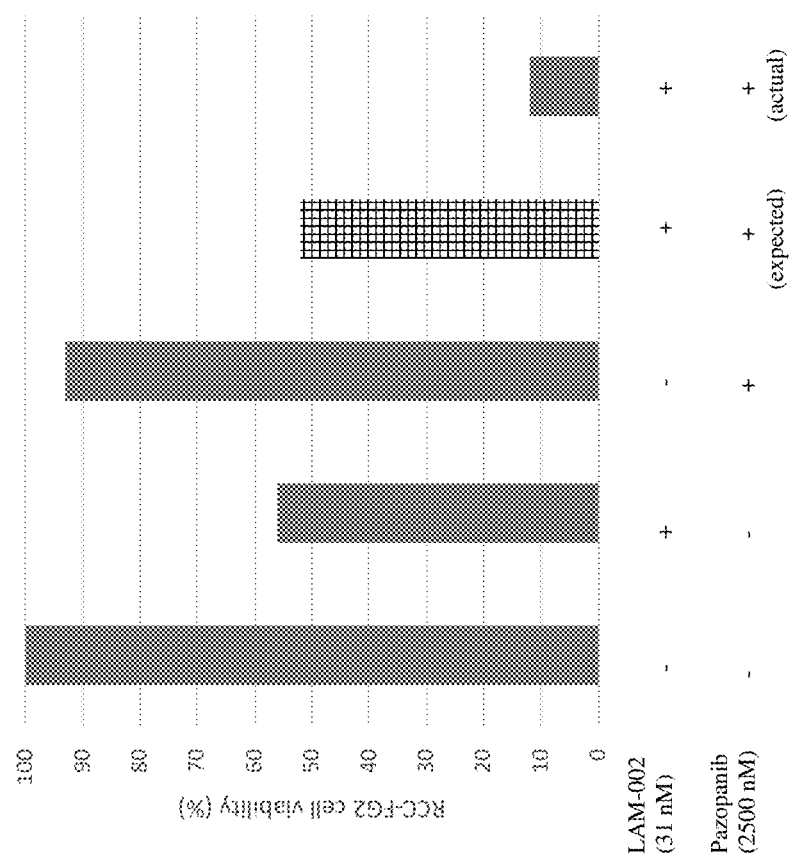
Figure 20B:
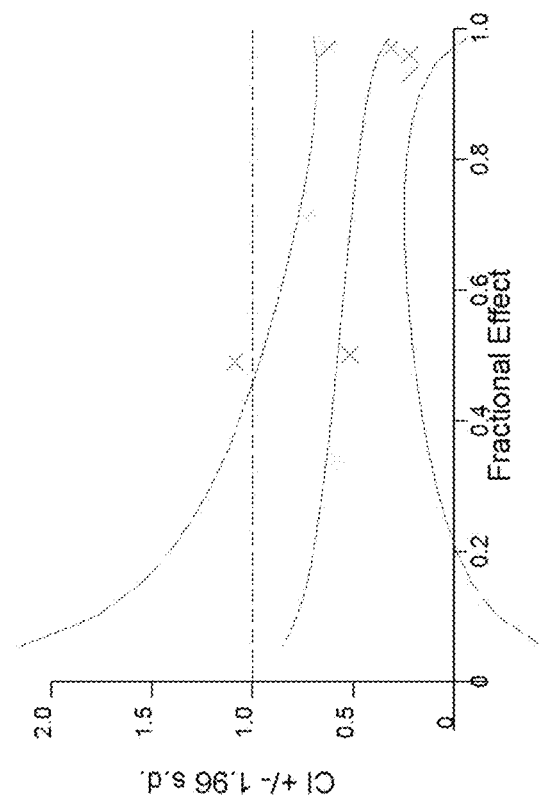
FIGS. 20A-B: LAM-002+pazopanib combination in RCC-MF cells (5 day assay). A, bar graph showing cell viability (%); B, determination of the combination index (CI) value at $ED_{50}$, $ED_{75}$ and $ED_{90}$.
Figure 20A:
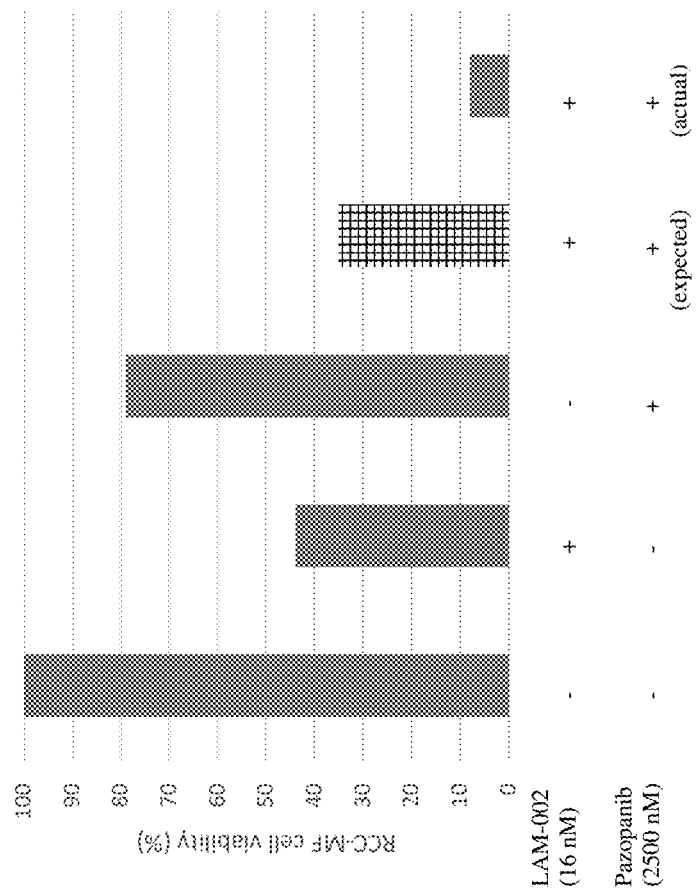
Figure 21B:
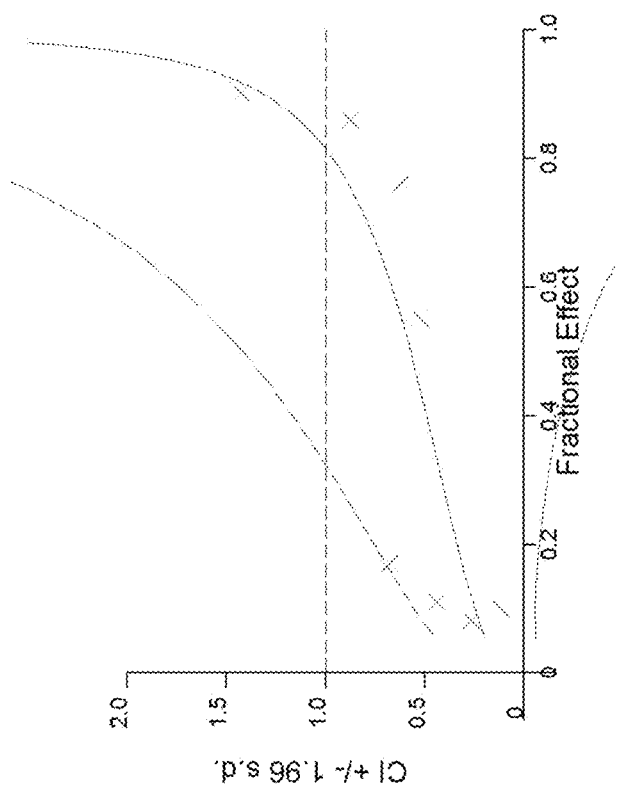
FIGS. 21A-B: LAM-002+pazopanib combination in 769-P cells (5 day assay). A, bar graph showing cell viability (%); B, determination of the combination index (CI) value at $ED_{50}$, $ED_{75}$ and $ED_{90}$.
Figure 21A:
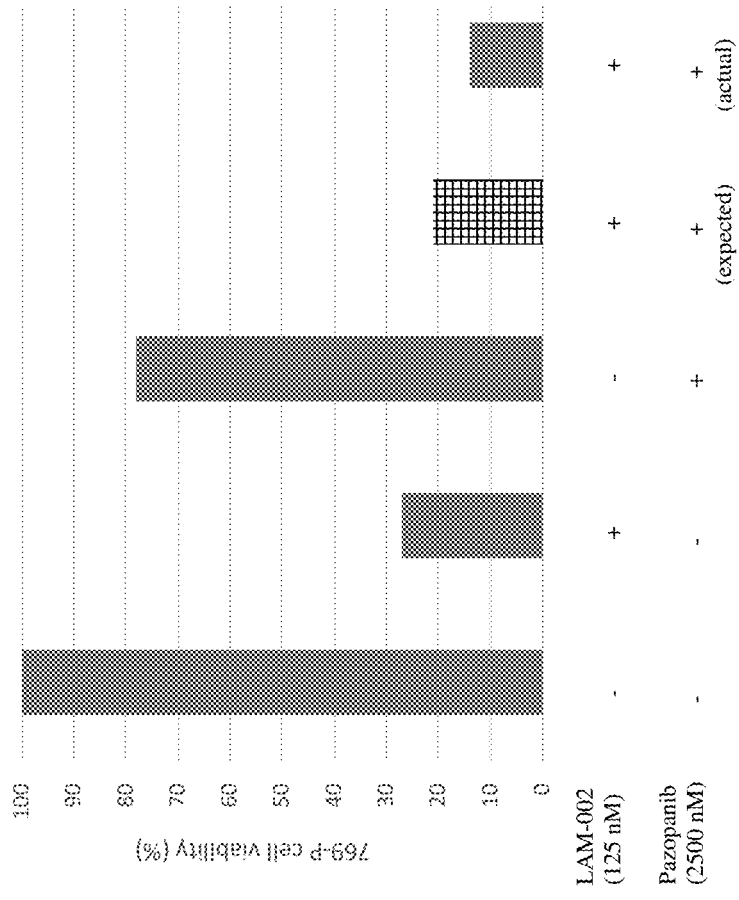

In a separate study, protein kinase profiling of apilimod was conducted to identify kinase targets (DiscoveRx, Fremont, Calif.). A dissociation constant (K$_d$) study was performed using apilimod at increasing concentrations (0.05-3000 nM) against PIKfyve, a known target of apilimod. The experiment was performed in duplicate and the K$_d$ was determined to be 0.075 nM (range 0.069-0.081 nM) (FIG. 5).

Next, apilimod was screened against a comprehensive panel of kinases (PIKfyve not included). In total, 456 kinases, including disease-relevant kinases, were assayed for their ability to bind with apilimod. The screening concentration of apilimod was 1 μM, a concentration that is >10,000 times greater than the K$_d$ for apilimod against PIKfyve. The results from the screen showed that apilimod did not bind to any of the 456 kinases tested.

Together, these results demonstrate that apilimod binds with high selectivity in cancer cells to a single cellular kinase, PIKfyve. PIKfyve is an enzyme that binds to PI(3)P and catalyzes the formation of the lipid second messengers PI(3,5)P2 and PI(5)P and others have shown that apilimod is also a potent and specific inhibitor of this kinase PIKfyve in normal cells. Cai X et al., Chem Biol. 2013 Jul. 25; 20(7):912-21. As discussed in more detail below, in order to understand the mechanism of apilimod's selective cytotoxicity against cancer cells, we conducted a series of experiments aimed at elucidating its biological activity in cancer cells.

Example 4: Mechanism of Anti-Cancer Activity of Apilimod

Apilimod was known to be a potent inhibitor of the inflammatory cytokines IL-12 and IL-23. To the extent apilimod was indicated for treating a disease or disorder, it was predicated on this activity. Although the clinical testing of apilimod focused on its potential efficacy in autoimmune and inflammatory diseases such as psoriasis, rheumatoid arthritis, and Crohn's disease, there were a few published suggestions that apilimod might be useful against cancers, and specifically against cancers in which c-rel or IL-12/23 were acting as pro-proliferative factors. See e.g., WO 2006/128129 and Baird et al., *Frontiers in Oncology* 3:1 (2013), respectively. Surprisingly, and contrary to these expectations predicated on apilimod's IL-12/23 inhibitory activity, we found no correlation between any of c-Rel expression (c-Rel is a transcription factor for the IL-12/23 genes), IL-12, or IL-23 expression and sensitivity to apilimod in the tested cell lines.

The expression of IL-12A, IL-12RB1, IL-12RB2, IL-12B, IL-23A and IL-23R was analyzed in a diverse group of 75 cancer cell lines (see Table 3).

TABLE 3

Various Cancer cell lines

| Number | Cancer Model | Cell Line | IC50 (nM) |
|---|---|---|---|
| 1 | Human Burkitt's lymphoma | ST486 | 25 |
| 2 | Human Mantle Cell Lymphoma | JeKo-1 | 70 |
| 3 | Human Diffuse Large B Cell Lymphoma -GCB | SUDHL-4 | 25 |
| 4 | Human Diffuse Large B Cell Lymphoma -GCB | SUDHL-6 | 80 |
| 5 | Human Burkitt's lymphoma | Daudi | 200 |
| 6 | Human histiocytic lymphoma | U937 | 106 |
| 7 | Human lung carcinoma | A549 | 110 |
| 8 | Human colorectal cancer | HCT116 | 125 |
| 9 | Human B-cell lymphoma | DB | 150 |
| 10 | Human Diffuse Large B Cell Lymphoma -GCB | WSU-DLCL2 | 160 |
| 11 | Human Colorectal | HCT-15 | 200 |
| 12 | Human Colorectal | SW480 | 90 |
| 13 | Human Colorectal | COLO-205 | 380 |
| 14 | Human Colorectal | SW620 | 90 |
| 15 | Human T-cell leukemia | Jurkat | 200 |
| 16 | Human neuroglioma | H4 | 250 |
| 17 | Human Diffuse Large B Cell Lymphoma -GCB | Toledo | 270 |
| 18 | Human B cell Non-Hodgkin's Lymphoma | Rec-1 | 300 |
| 19 | Human Hodgkin's lymphoma | KMH-2 | 181 |
| 20 | Human Burkitt's lymphoma | EB1 | 174 |
| 21 | Human Diffuse Large B Cell Lymphoma -GCB | SUDHL-10 | 20 |
| 22 | Human Burkitt's lymphoma | GA-10 | 382 |
| 23 | Human Diffuse Large B Cell Lymphoma -GCB | OCI-Ly19 | 380 |
| 24 | Human Diffuse Large B Cell Lymphoma -GCB | HT | 642 |
| 25 | Human Diffuse Large B Cell Lymphoma -GCB | Pfeiffer | 2,620 |
| 26 | Human Burkitt's lymphoma | Namalwa | 600 |
| 27 | Human Follicular B Cell Lymphoma-GCB | DOHH-2 | 700 |
| 28 | Human Bladder carcinoma (GATOR−/−) | SW780 | 1000 |
| 29 | Human colorectal cancer | MDST8 | 1000 |
| 30 | Human Burkitt's lymphoma | Raji | 10,000 |
| 31 | Human Hodgkin's lymphoma | HD-MyZ | >1000 |
| 32 | Human Hodgkin's lymphoma | L540 | >1000 |
| 33 | Human Hodgkin's lymphoma | HDLM-2 | >1000 |
| 34 | Human Burkitt's lymphoma | CA46 | >10,000 |
| 35 | Human Anaplastic Large Cell Lymphoma | SUDHL-1 | 590 |
| 36 | Human lung carcinoma | H1734 | 1500 |
| 37 | Human colorectal cancer | SW1116 | 1500 |
| 38 | Human Colorectal | COLO-320DM | 2,060 |
| 39 | Human neuroblastoma | A172 | 2000 |
| 40 | Human lung carcinoma | H1693 | 2000 |
| 41 | Human lung carcinoma | H460 | >2000 |
| 42 | Human lung carcinoma | H358 | >2000 |
| 43 | Human pancreatic cancer | CAPAN2 | >2000 |
| 44 | Human pancreatic cancer | PANC1 | >2000 |
| 45 | Human pancreatic cancer | MiaPaCa-2 | >2000 |
| 46 | Human pancreatic cancer | AsPC1 | >2000 |
| 47 | Human prostate cancer | DU145 | >2000 |
| 48 | Human acute myelogenous leukemia | KG-1 | >2500 |
| 49 | Human prostate cancer | LnCap | 3000 |
| 50 | Human T-cell lymphoma | HH | 3,300 |
| 51 | Human T-cell leukemia | MOLT-4 | 3,300 |

TABLE 3-continued

Various Cancer cell lines

| Number | Cancer Model | Cell Line | IC50 (nM) |
|---|---|---|---|
| 52 | Human prostate cancer | 22RV1 | >5000 |
| 53 | Human colorectal cancer | DLD-1 | >5000 |
| 54 | Human myelogenous leukemia | K562 | >5000 |
| 55 | Human colorectal cancer | RKO | >5000 |
| 56 | Human ovarian | TOV-21G | 7000 |
| 57 | Human prostate cancer | PC-3 | 10,000 |
| 58 | Human Hodgkin's lymphoma | L428 | 10,000 |
| 59 | Human plasmacytoma | RPMI-8226 | >10,000 |
| 60 | Human lung carcinoma | NCI-1975 | >10,000 |
| 61 | Human breast cancer | CAMA1 | >10,000 |
| 62 | Human neuroblastoma | SW1088 | >10,000 |
| 63 | Human neuroblastoma | M0591K | >10,000 |
| 64 | Human neuroblastoma | U-118 MG | >10,000 |
| 65 | Human neuroblastoma | U-87 MG | >10,000 |
| 66 | Human acute monocytic leukemia | THP1 | >10,000 |
| 67 | Human Diffuse Large B Cell Lymphoma -GCB | KARPAS-422 | >10,000 |
| 68 | Human Follicular B Cell Lymphoma | RL | >10,000 |
| 69 | Human Mantle Cell Lymphoma | GRANTA-519 | >10,000 |
| 70 | Human bronchioalveolar | NCI-H1650 | >20,000 |
| 71 | Human bronchioalveolar | SW1573 | >20,000 |
| 72 | Human bronchioalveolar | NCI-H1781 | >20,000 |
| 73 | Human bronchioalveolar | NCI-H1666 | 20,000 |
| 74 | Human Colorectal | LOVO | >10,000 |
| 75 | Human Colorectal | HT-29 | >10,000 |

Briefly, gene expression data from the CCLE was analyzed for the 75 cancer cell lines for which dose response curves against apilimod were obtained. The expression of each interleukin gene was compared in sensitive ($IC_{50}$ less than 500 nM) and insensitive ($IC_{50}$ greater than 500 nM) lines by unpaired t-test. No statistically significant relationship was found with the sole exception of IL-23A (p=0.022). IL-23A has been previously noted to be elevated in apilimod sensitive non small cell lung cancer lines, and recombinant IL-23A was noted to increase proliferation of non small cell lung cancer lines (see Baird et al. 2013, supra). Importantly, the statistical significance of IL-23A expression in sensitive cancer lines appears to be driven entirely by just two colon cancer lines. Furthermore IL-23A expression is not a statistically significant predictor of sensitivity in Non-Hodgkin's B cell lymphoma.

Example 5: Apilimod Inhibits Proliferation of Renal Cancer Cells

The renal cancer cell lines RCC-MF, RCC-ER, RCC-JF, and RCC-JW were grown in McCoy's 5A medium (Corning), while 786-0, 769-P and RCC-FG2 were grown in RPMI-1640 (Corning) and A-704 were grown in MEM (Corning) supplemented with 10% FBS (Sigma Aldrich F2442-500ML, Lot 12D370) and Penicillin/Streptomycin (100×) (CellGro Ref 30-002) and seeded at a density of 1000, 1200, 1000, 4000, 200, 2000, 1200 and 5000 cells per well, respectively, into 96 well plates in a final volume of 50 μL.

For single treatment studies, 24 h after seeding, cells were treated with apilimod mesylate (referred to in this example as simply 'apilimod' or LAM-002), sorafenib, pazopanib or sunitinib at a final concentration 0.5-10000 nM (3-fold dilutions and a total of 10 dilutions). All drug dilutions were made up as a 2× stock and 50 μL added to appropriate wells. Cells were treated for 120 h before viability was assessed using CellTiterGlo® (Promega) where the relative luminescence of untreated cells was set to 100% viability and each drug concentration expressed as a percentage of untreated cells. $EC_{50}$ values were determined using GraphPad Prism (GraphPad Software, Inc). Briefly, raw data was log transformed and then analyzed using nonlinear regression (curve fit) where the data were constrained (bottom=0, top=100).

The results of these single treatment studies are shown in FIGS. 6-13 and summarized in the following table.

TABLE 4

Results of single treatment studies in renal cancer cell lines

| Cell line | IC50 (nM) |
|---|---|
| 769-P | 44 |
| RCC-MF | 8 |
| RCC-ER | 9 |
| RCC-FG2 | 32 |
| RCC-JF | 60 |
| 786-0 | 71 |
| A-704 | 11 |
| RCC-JW | 27 |

For calculation of synergy between apilimod and pazopanib, or sorafenib, RCC-ER, RCC-FG2, RCC-MF, and 769-P cells were seeded as outlined above. 24 h later, cells were treated with apilimod alone (final concentration 2-250 nM; 2-fold dilutions and a total of 8 dilutions), with pazopanib alone (final concentration 78.1-10000 nM; 2-fold dilutions and a total of 8 dilutions) or with sorafenib (final concentration 78.1-10000 nM; 2-fold dilutions and a total of 8 dilutions) or the combination of each concentration of apilimod with each concentration of pazopanib or of sorafenib (8×8 matrix). Cells were treated for 120 h before viability was assessed using CellTiterGlo® (Promega) where the relative luminescence of untreated cells was set to 100% viability and each drug concentration expressed as a percentage of untreated cells.

FIGS. 14-21 show the results of the synergy studies. Bar graphs in each figure (A) show the effect of a single concentration of apilimod, a single concentration of pazopanib and the effect of the combination of apilimod and pazopanib (at the single agent concentrations) on cell viability. The 'expected value', if the combinatorial effects of the two drugs were additive, was calculated by using the fraction of viability for apilimod multiplied by fraction of viability for pazopanib, and is shown as the black bar. The CI versus fractional effect graphs (B) in each figure show the combination index (CI) as defined by Chou et al. (Chou TC, Talalay P. Quantitative analysis of dose-effect relationships: the combined effects of multiple drugs or enzyme inhibitors. *Adv Enzyme Regul.* 1984; 22:27-55) which was used as a measure of synergy and calculated using CalcuSyn (version 2.11, Biosoft). The analysis was constrained to assess CI values which were within a clinically achievable concentration and also where the fraction effect (Fa) was greater than 0.75 (i.e., a greater than 75% reduction in cell viability with the combination of drugs). In the CI versus fractional effect graphs datapoints are denoted by 'x' and lines show 95% confidence interval, and drug combinations producing CI values>1 are antagonistic, CI=1 are additive, and CI<1 are synergistic. In addition, the CI value at the $ED_{50}$, $ED_{75}$ and $ED_{90}$ are shown for the combination of apilimod and either pazopanib or sorafenib. The same methodology was applied for the combination of apilimod with sorafenib. Tables 6 below summarizes the results of the synergy studies.

The data presented here demonstrate that apilimod was able to act synergistically with pazopanib and with sorafenib in the panel of renal cell lines tested.

TABLE 5

CI value at the $ED_{50}$, $ED_{75}$ and $ED_{90}$ for the combination of apilimod and pazopanib in various cell lines.

| Cell Line | Apilimod+ | CI at $ED_{50}$ | CI at $ED_{75}$ | CI at $ED_{90}$ |
|---|---|---|---|---|
| RCC-ER | sorafenib | 0.77 | 0.45 | 0.31 |
| RCC-FG2 | sorafenib | 0.79 | 0.64 | 0.51 |
| RCC-MF | sorafenib | 0.73 | 0.59 | 0.48 |
| 769-P | sorafenib | 1.22 | 0.87 | 0.62 |
| RCC-ER | pazopanib | 0.56 | 0.35 | 0.22 |
| RCC-FG2 | pazopanib | 0.32 | 0.38 | 0.46 |
| RCC-MF | pazopanib | 0.58 | 0.50 | 0.43 |
| 769-P | pazopanib | 0.57 | 0.87 | 1.31 |

TABLE 6

Summary of synergy studies.

| | RCC-ER | RCC-FG2 | RCC-MF | 769-P |
|---|---|---|---|---|
| Pazopanib + LAM-002 | Synergistic | Synergistic | Synergistic | Synergistic |
| Sorafenib + LAM-002 | Synergistic | Synergistic | Synergistic | Synergistic |

What is claimed is:

1. A method for treating clear cell renal carcinoma in a subject in need thereof, the method comprising administering to the subject a pharmaceutical composition comprising a therapeutically effective amount of apilimod, or a pharmaceutically acceptable salt thereof.

2. The method of claim 1, wherein the clear cell renal carcinoma is refractory to standard treatment or is metastatic.

3. The method of claim 1, wherein the composition is in a form suitable for oral or intravenous administration.

4. The method of claim 1, wherein the pharmaceutically acceptable salt is selected from sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate.

5. The method of claim 4, wherein the pharmaceutically acceptable salt is selected from chloride, phosphate, lactate, tartrate, maleate, fumarate, methanesulfonate, and pamoate.

6. The method of claim 1, further comprising administering to the subject at least one additional active agent.

7. The method of claim 6, wherein the at least one additional active agent is a vascular endothelial growth factor (VEGF) inhibitor.

8. The method of claim 7, wherein the VEGF inhibitor is selected from the group consisting of bevacizumab, sunitinib, pazopanib, axitinib, sorafenib, regorafenib, lenvatinib, motesanib, and vandetanib.

9. The method of claim 8, wherein the VEGF inhibitor is selected from pazopanib or sorafenib, or a combination thereof.

10. The method of claim 6, wherein the at least one additional active agent is a PD-1/PDL-1 pathway inhibitor.

11. The method of claim 10, wherein the at least one additional active agent is selected from pembrolizumab, avelumab, atezolizumab (MPDL3280A), nivolumab (BMS-936558), pidilizumab (MK-3475), MSB0010718C, and MEDI4736.

\* \* \* \* \*